US012735403B2

(12) United States Patent
Zhao et al.

(10) Patent No.: US 12,735,403 B2
(45) Date of Patent: Sep. 15, 2026

(54) SALT OF Rho-ASSOCIATED PROTEIN KINASE INHIBITOR, SOLID FORM OF THE SALT, PREPARATION METHOD FOR SAME, AND USES THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Zewang Feng, Beijing (CN); Nana Tian, Beijing (CN); Lai Wei, Beijing (CN); Xiangrong Cao, Beijing (CN); Jie Chen, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 656 days.

(21) Appl. No.: 18/023,394

(22) PCT Filed: Aug. 30, 2021

(86) PCT No.: PCT/CN2021/115198

§ 371 (c)(1),
(2) Date: Feb. 27, 2023

(87) PCT Pub. No.: WO2022/042712

PCT Pub. Date: Mar. 3, 2022

(65) Prior Publication Data

US 2023/0312530 A1 Oct. 5, 2023

(51) Int. Cl.
*C07D 403/14* (2006.01)

(52) U.S. Cl.
CPC ........ *C07D 403/14* (2013.01); *C07B 2200/13* (2013.01)

(58) Field of Classification Search
CPC .................................................... C07D 403/14
See application file for complete search history.

(56) References Cited

U.S. PATENT DOCUMENTS 11,390,609 B2 * 7/2022 Zhao .................... A61K 31/506

FOREIGN PATENT DOCUMENTS

| | | |
|---|---|---|
| JP | 2020525522 | 8/2020 |
| WO | 2019001572 | 1/2019 |
| WO | 2020177587 | 9/2020 |
| WO | 2020259528 | 12/2020 |
| WO | 2023041026 | 3/2023 |

OTHER PUBLICATIONS

Hilfiker R., Blatter F., von Raumer M.: "Relevance of Solid-state Properties for Pharmaceutical Products" In: Hifiker, R.: "Polymorphism in the Pharmaceutical Industry", Jan. 2006 (Jan. 2006), Wiley-VCH, Weinheim, ISBN: 978-3-527-31146-0, pp. 1-19.
Bastin, R.J. et al., "Salt Selection and Optimisation Procedures for Pharmaceutical New Chemical Entities", Organic Process Research & Development, 2000, 4(5), p. 427-435.
Balbach, S. et al., 'Pharmaceutical evaluation of early development candidates "The 100 mg approach"', International Journal of Pharmaceutics, 2004, 275, p. 1-12.
Kazuhide Ashizawa et al., Polymorphism and Crystallization of Pharmaceuticals, Maruzen Planet Co., Ltd., Sep. 20, 2002, pp. 305-317.
Yoko Kawaguchi et al., Life Engineering Research, 2002, vol. 4, No. 2, pp. 310-317.
Edited by Noriaki Hirayama, Organic Compound Crystallization Handbook-Principles and Know-how-, Maruzen Co., Ltd., 2008, pp. 57-84.
Mitsuhisa Yamano, "Approach to Crystal Polymorph in Process Research of New Drug", Journal of Synthetic Organic Chemistry, Sep. 1, 2007, vol. 65, No. 9, p. 907(69)-913(75).
Noriyuki Takada, Screening and Selection of Drug Substance Form in Drug Development Process, Pharm Stage, vol. 6, No. 10, Jan. 15, 2007, p. 20-25.

* cited by examiner

*Primary Examiner* — Brian E Mcdowell
(74) *Attorney, Agent, or Firm* — Robin L. Teskin; Baker, Donelson, Bearman, Caldwell & Berkowitz PC

(57) ABSTRACT

The present invention relates to a salt of (6-(4-((4-(1H-pyrazol-4-yl)phenyl)amino)pyrimidin-2-yl)-1-methyl-1H-indol-2-yl)(3,3-difluoroazetidine-1-yl)methanone (herein referred to as "compound A"), a solid form of the salt, a method for preparing the solid form, a pharmaceutical composition comprising the solid form, and uses of the solid form as a Rho-associated protein kinase (ROCK) inhibitor, preferably a selective ROCK2 inhibitor.

Compound A

10 Claims, 10 Drawing Sheets

SALT OF Rho-ASSOCIATED PROTEIN KINASE INHIBITOR, SOLID FORM OF THE SALT, PREPARATION METHOD FOR SAME, AND USES THEREOF

CROSS-REFERENCE TO RELATED APPLICATIONS

This application is a U.S. Nat'l Phase application of Int'l Appl. No. PCT/CN2021/115198, filed Aug. 30, 2021, which claims priority to Int'l Appl. No. PCT/CN2020/112500, filed Aug. 31, 2020, each of which are incorporated herein by reference in their entireties.

FIELD OF THE INVENTION

The present invention relates to a salt of (6-(4-((4-(1H-pyrazol-4-yl)phenyl)amino)pyrimidin-2-yl)-1-methyl-1H-indol-2-yl)(3,3-difluoroazetidine-1-yl)methanone (hereinafter referred to as "compound A"), a solid form of the salt, a method for preparing the solid form, a pharmaceutical composition comprising the solid form, and uses of the solid form as a Rho-associated protein kinase (ROCK) inhibitor, preferably a selective ROCK2 inhibitor.

BACKGROUND OF THE INVENTION

Rho-associated protein kinase (ROCK) is a serine/threonine kinase from the AGC kinase family, and comprises two isoforms, ROCK1 and ROCK2. ROCK1 and ROCK2 are expressed and regulated differently in specific tissues. For example, ROCK1 is ubiquitously expressed at a relatively high level, while ROCK2 is preferentially expressed in heart, brain and skeletal muscle. ROCK is the first downstream effector of the Rho protein discovered, and its biological function is achieved by phosphorylating the downstream effector proteins (MLC, Lin-11, Isl-1, LIMK, ERM, MARCKS, CRMP-2, etc.). Studies have shown that various diseases (e.g., pulmonary fibrosis, cardiac-cerebral vascular disease, neurological disease and cancer etc.) are related to the pathways mediated by ROCK. As such, ROCK is considered as an important target in the development of novel drugs.

The applicant has discovered that (6-(4-((4-(1H-pyrazol-4-yl)phenyl)amino)pyrimidin-2-yl)-1-methyl-1H-indol-2-yl)(3,3-difluoroazetidin-1-yl)methanone can be used as a potent Rho-associated protein kinase (ROCK) inhibitor (see PCT/CN2018/093713, which is incorporated herein by reference in its entirety), but salts of the compound and solid forms thereof have not yet been reported.

SUMMARY OF THE INVENTION

In one aspect, the present invention provides a salt of compound A ((6-(4-((4-(1H-pyrazol-4-yl)phenyl)amino)pyrimidin-2-yl)-1-methyl-1H-indol-2-yl)(3,3-difluoroazetidin-1-yl)methanone) as shown below:

Compound A

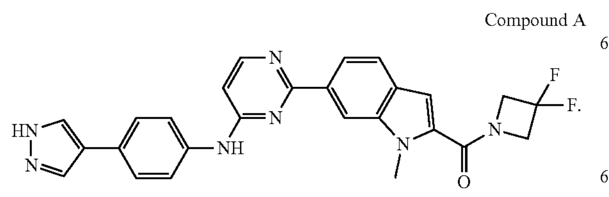

In another aspect, the present invention provides crystalline forms of the compound A salts and solvates thereof.

The preferred crystalline forms of the present invention not only have an excellent effect in preventing or treating a disease mediated by the Rho-associated protein kinase (ROCK), but also have other advantages. For example, the preferred crystalline forms of the present invention have excellent physical properties (including solubility, dissolution rate, light resistance, low hygroscopicity, high temperature resistance, high humidity resistance, fluidity, and the like), and the preferred crystalline forms of the present invention may have superior properties in terms of bioavailability, physical and/or chemical stability, and ease of preparation. The preferred crystalline forms of the present invention have good powder properties, are more suitable and convenient for mass production and for forming a formulation, can reduce irritation and enhance absorption, solve problems in metabolic rates, significantly decrease toxicity resulted from drug accumulation, improve safety, and effectively ensure the quality and efficacy of the pharmaceutical products.

In another aspect, the present invention provides methods for preparing the crystalline forms of the present invention.

In another aspect, the present invention provides a pharmaceutical composition comprising any one or more of the crystalline forms of the present invention and one or more pharmaceutically acceptable carriers.

In another aspect, the present invention provides use of the crystalline forms of the present invention in the manufacture of a medicament as a Rho-associated protein kinase (ROCK) inhibitor, preferably selective ROCK2 inhibitor.

DETAILED DESCRIPTION OF THE INVENTION

Definitions

Figure 1:
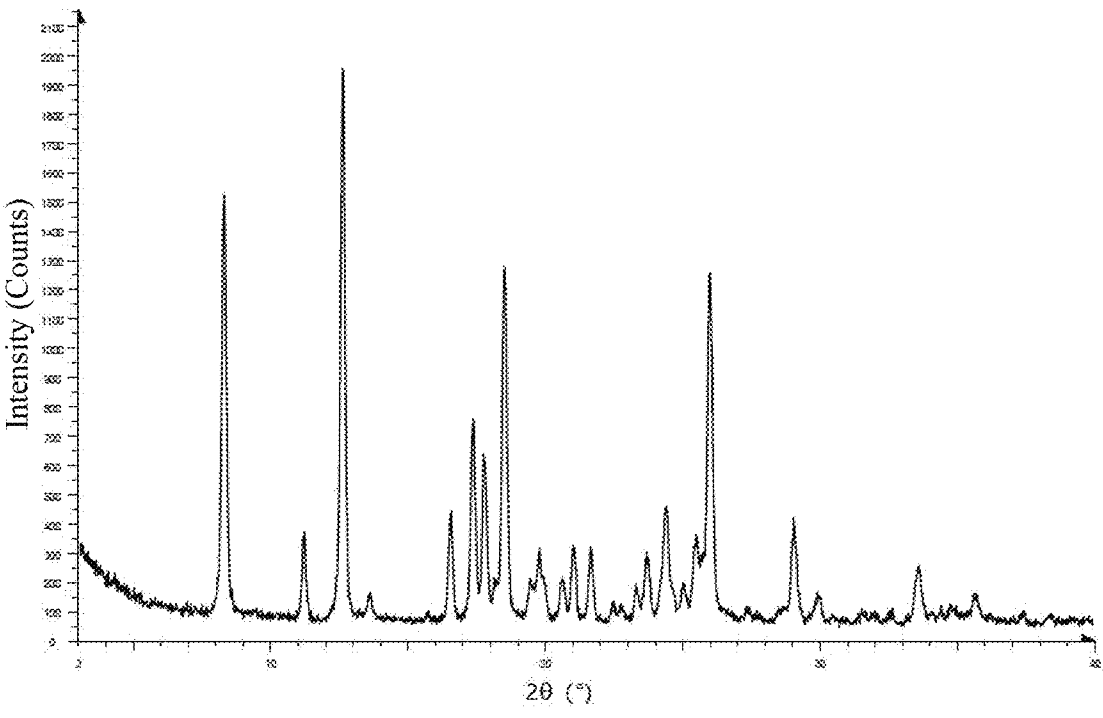
FIG. 1 is an X-ray powder diffraction (XRPD) pattern of crystalline form I of compound A monohydrochloride monohydrate.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The word "about" as used herein refers to, as appreciated by a person skilled in the art, a range within the acceptable standard error of a value, such as ±0.05, ±0.1, ±0.2, ±0.3, ±1, ±2 or ±3, etc.

The term "solid form" as used herein includes all solid forms of compound A or any solvate thereof, such as a crystalline form or amorphous form.

The term "amorphous" as used herein refers to any solid substance which lacks order in three dimensions. In some instances, amorphous solids may be characterized by known techniques, including XRPD crystallography, solid state nuclear magnet resonance (ssNMR) spectroscopy, DSC, or some combination of these techniques. As illustrated below, amorphous solids give diffuse XRPD patterns, typically comprised of one or two broad peaks (i.e., peaks having base widths of about 5° 2θ or greater).

The term "crystalline form" or "crystal" as used herein refers to any solid substance exhibiting three-dimensional order, which in contrast to an amorphous solid substance, gives a distinctive XRPD pattern with sharply defined peaks.

The term "X-ray powder diffraction pattern (XRPD pattern)" as used herein refers to the experimentally observed diffractogram or parameters derived therefrom. XRPD patterns are usually characterized by peak positions (abscissa) and peak intensities (ordinate).

The term "2θ" as used herein refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein. For example, as described herein, Cu-Kα (Kα1 (Å): 1.540598 and Kα2 (Å): 1.544426 Å) was used as the source of radiation.

As used herein, "1%" refers to the percentage of peak intensity.

The term "differential scanning calorimetry (DSC) graph" as used herein refers to a curve recorded on a differential scanning calorimeter.

The term "thermogravimetric analysis (TGA) graph" as used herein refers to a curve recorded on a thermogravimetric analyzer.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degree, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art. Similarly, as used herein, "essentially the same" with reference to the DSC graph is intended to also encompass the variabilities associated with these analytical techniques, which are known to those of skill in the art. For example, a differential scanning calorimetry graph will typically have a variability of up to ±0.2° C. for well defined peaks, and even larger for broad lines (e.g., up to ±1° C.).

The liquid nuclear magnetic resonance spectrum in the present application is preferably collected on a Bruker Advance 300 nuclear magnetic resonance spectrometer, with DMSO-$d_6$ as the solvent, unless otherwise stated.

The polarization microscopy data in the present application is preferably collected on Polarizing Microscope ECLIPSE LV100POL (Nikon, JPN).

Numerical ranges (e.g., "1 to 10", "1 to 6", "2 to 10", "2 to 6", "3 to 10", "5 to 10", "3 to 6"), etc. as used herein encompass any point within the numerical range (for example, 1, 2, 3, 4, 5, 6, 7, 8, 9, or 10).

The prepared salt or crystalline form thereof may be recovered by methods including decantation, centrifugation, evaporation, gravity filtration, suction filtration, or any other technique for the recovery of solids under pressure or under reduced pressure. The recovered solid may optionally be dried. "Drying" in the present invention is carried out under reduced pressure (preferably in vacuum) until the residual solvent content is lowered within the limits given in the International Conference on Harmonisation of Technical Requirements for Registration of Pharmaceuticals for Human Use ("ICH") guidelines. The residual solvent content depends on the type of the solvent, but does not exceed about 5000 ppm, or preferably about 4000 ppm, or more preferably about 3000 ppm. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure (preferably in vacuum) for any desired period (e.g., about 1, 2, 3, 5, 10, 15, 20, 24 hours or overnight) until the desired result is achieved, as long as the salt is not degraded in quality. The drying can be carried out any desired times until the desired product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

The term "anhydrous" as used herein preferably means a crystalline form in which no water molecule is comprised as a structural element.

Salt of Compound a, Crystalline Form Thereof and Preparation Method Therefor

In some embodiments, the present invention provides a salt of compound A,

Compound A

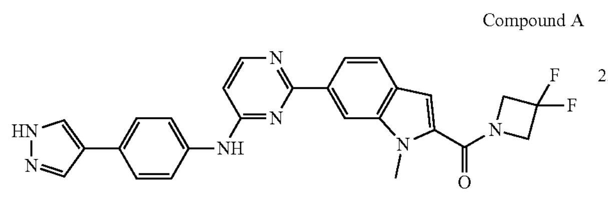

which is an inorganic acid salt or an organic acid salt.

In preferred embodiments, the present invention provides a salt of compound A, which is compound A hydrochloride;

preferably, the compound A hydrochloride is compound A monohydrochloride;

preferably, the compound A hydrochloride is crystalline form I of compound A monohydrochloride monohydrate;

the crystalline form I has an XRPD pattern comprising characteristic peaks at diffraction angles (2θ) of about 8.3±0.2°, 12.6±0.2° and 18.5±0.2°;

preferably comprising characteristic peaks at diffraction angles (2θ) of about 8.3±0.2°, 12.6±0.2°, 16.5±0.2°, 17.3±0.2°, 17.8±0.2°, 18.5±0.2°, 24.4±0.2°, 26.0±0.2° and 29.1±0.2°;

most preferably comprising characteristic peaks at diffraction angles (2θ) of about 8.3±0.2°, 11.2±0.2°, 12.6±0.2°, 16.5±0.2°, 17.3±0.2°, 17.8±0.2°, 18.5±0.2°, 19.5±0.2°, 19.8±0.2°, 20.6±0.2°, 21.0±0.2°, 21.7±0.2°, 23.7±0.2°, 24.4±0.2°, 25.5±0.2°, 26.0±0.2°, 29.1±0.2° and 33.6±0.2°.

In more preferred embodiments, the crystalline form I has an XRPD pattern comprising peaks at the following diffraction angles (2θ):

| Peak No. | 2θ(°) ± 0.2° | I % |
|---|---|---|
| 1 | 8.3 | 78.1 |
| 2 | 11.2 | 18.7 |
| 3 | 12.6 | 100 |
| 4 | 13.6 | 8.3 |
| 5 | 15.7 | 4.9 |
| 6 | 16.5 | 22.5 |
| 7 | 17.3 | 38.6 |
| 8 | 17.8 | 31.5 |
| 9 | 18.5 | 65.3 |

-continued

| Peak No. | 2θ(°) ± 0.2° | I % |
|---|---|---|
| 10 | 19.5 | 10.6 |
| 11 | 19.8 | 15.9 |
| 12 | 20.6 | 10.7 |
| 13 | 21.0 | 15.9 |
| 14 | 21.7 | 15.7 |
| 15 | 22.5 | 6.5 |
| 16 | 22.8 | 5.9 |
| 17 | 23.3 | 9.5 |
| 18 | 23.7 | 15.3 |
| 19 | 24.4 | 23.2 |
| 20 | 25.0 | 9.7 |
| 21 | 25.5 | 18.2 |
| 22 | 26.0 | 64.2 |
| 23 | 27.4 | 5.5 |
| 24 | 29.1 | 21.3 |
| 25 | 30.0 | 8.2 |
| 26 | 31.6 | 4.6 |
| 27 | 32.0 | 4.9 |
| 28 | 32.6 | 4.1 |
| 29 | 33.6 | 13 |
| 30 | 34.4 | 5.9 |
| 31 | 34.8 | 6 |
| 32 | 35.7 | 7.1 |
| 33 | 37.4 | 4.9 |
| 34 | 38.4 | 4.4 |
| 35 | 39.8 | 3.5 |

In more preferred embodiments, the crystalline form I has an XRPD pattern comprising peaks at diffraction angles (2θ) essentially the same as shown in FIG. 1. In the most preferred embodiment, the XRPD pattern of crystalline form I is essentially the same as shown in FIG. 1.

In more preferred embodiments, the crystalline form I has a DSC graph comprising endothermic peaks at about 105° C., about 146° C. and about 245° C.

Figure 2:
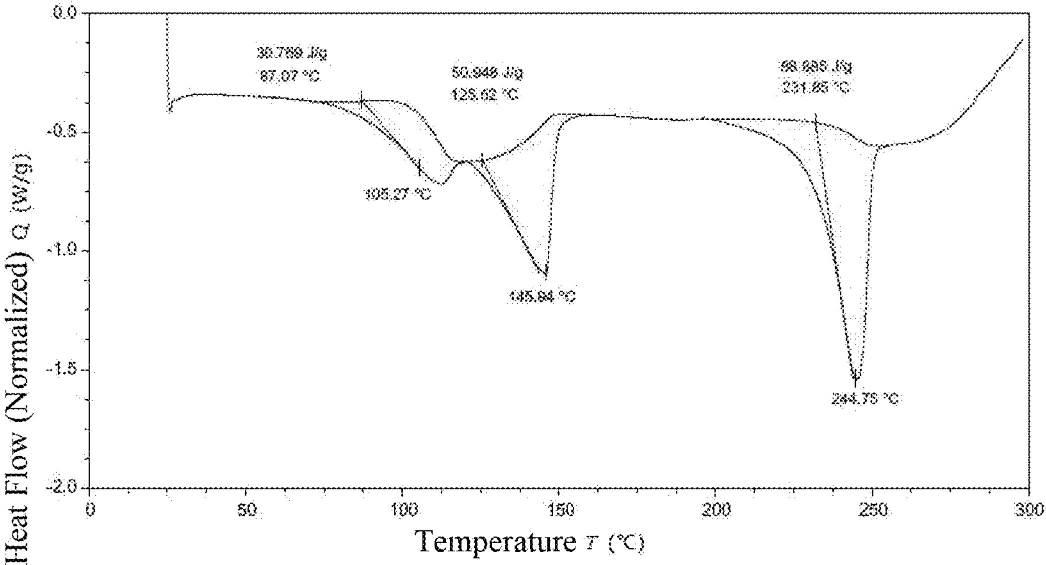
FIG. 2 is a differential scanning calorimetry (DSC) graph of crystalline form I of compound A monohydrochloride monohydrate.

In more preferred embodiments, the crystalline form I has a DSC graph comprising characteristic peaks essentially the same as shown in FIG. 2. In the most preferred embodiment, the crystalline form I has a DSC graph essentially the same as shown in FIG. 2.

In more preferred embodiments, in a thermogravimetric analysis, the crystalline form I has a weight loss of about 3.4% when heated to about 169° C.

The DSC graph of the crystalline form I has two consecutive endothermic peaks at 75-169° C., and the corresponding TGA graph shows a weight loss of about 3.4% before 169° C., indicating that the crystalline form I begins to lose water when the temperature is higher than 75° C.

Figure 3:
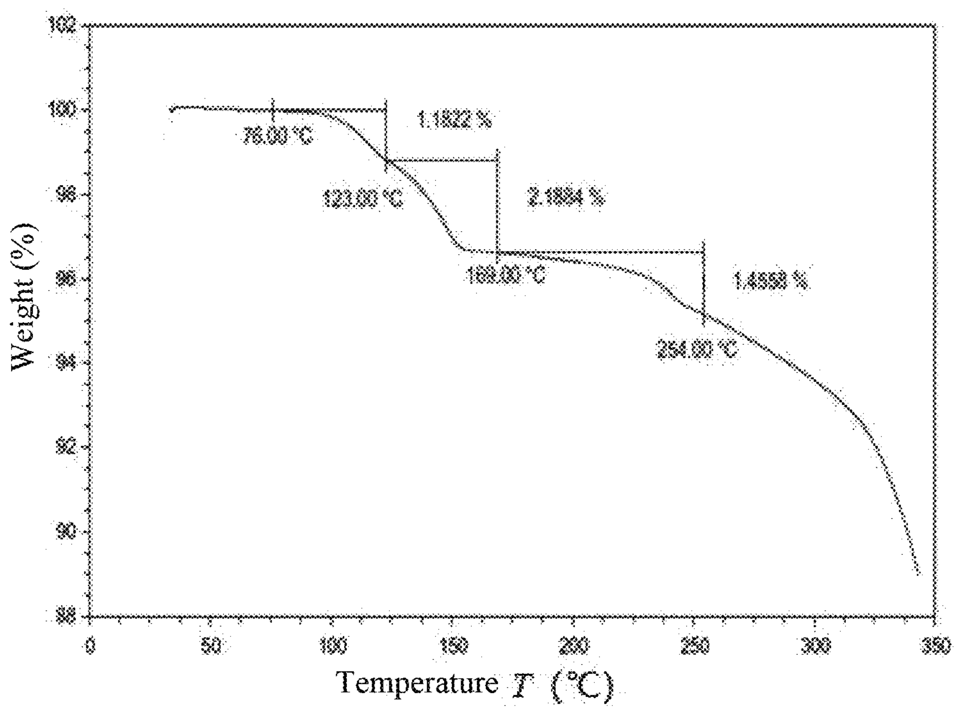
FIG. 3 is a thermogravimetric analysis (TGA) graph of crystalline form I of compound A monohydrochloride monohydrate.

In the most preferred embodiment, the crystalline form I has a TGA graph essentially the same as shown in FIG. 3.

Figure 4:
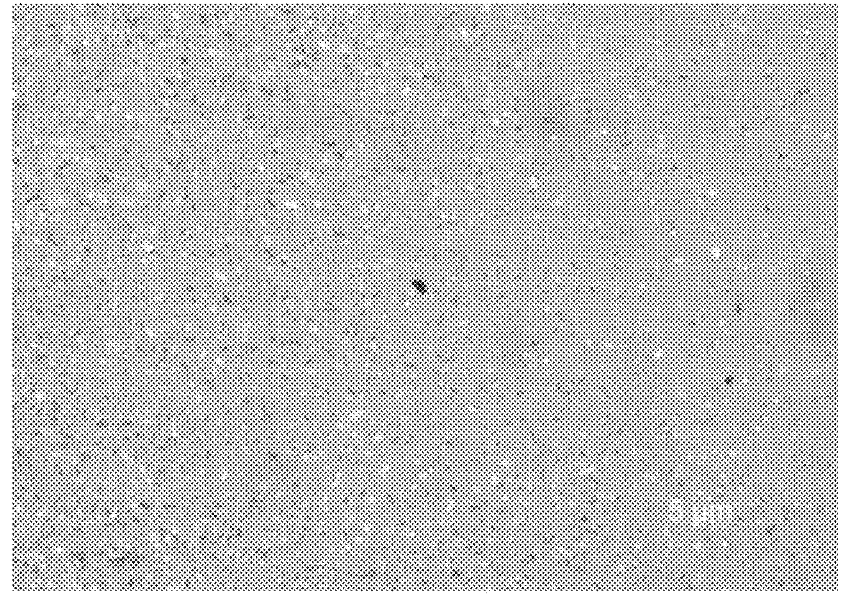
FIG. 4 is a scanning electron microscope image of crystalline form I of compound A monohydrochloride monohydrate.

In the most preferred embodiment, the crystalline form I has a scanning electron microscope image essentially the same as shown in FIG. 4.

In some embodiments, the present invention provides a method for preparing the crystalline form I, comprising adding a ketone solvent (preferably a ketone having 3-6 carbon atoms, including but not limited to acetone, butanone, methyl ethyl ketone, methyl isobutyl ketone and diethyl ketone) to compound A, stirring under heating (preferably heating to about 40-80° C., e.g., about 50° C. or about 60° C.), and then adding water (the volume ratio of the ketone solvent to water is preferably about (1-15):1, preferably about 10:1), so as to fully dissolve compound A; then adding hydrochloric acid (the concentration of hydrochloric acid is preferably 2-15 mol/L, preferably 12 mol/L (i.e., concentrated hydrochloric acid), and the molar ratio of compound A to HCl is 1:(1-1.3)), stirring under heating (preferably heating to about 40-80° C., e.g., about 50° C. or 60° C.), filtering and optionally drying to obtain the crystalline form.

In preferred embodiments, the compound A hydrochloride is crystalline form II of compound A monohydrochloride dihydrate;

the crystalline form II has an XRPD pattern comprising characteristic peaks at diffraction angles (2θ) of about 9.9±0.2°, 13.2±0.2° and 16.2±0.2°;

preferably comprising characteristic peaks at diffraction angles (2θ) of about 9.9±0.2°, 11.0±0.2°, 13.2±0.2°, 13.5±0.2°, 13.8±0.2°, 16.2±0.2°, 19.4±0.2° and 25.2±0.2°;

most preferably comprising characteristic peaks at diffraction angles (2θ) of about 6.5±0.2°, 9.9±0.2°, 11.0±0.2°, 11.6±0.2°, 11.8±0.2°, 13.2±0.2°, 13.5±0.2°, 13.8±0.2°, 16.2±0.2°, 16.6±0.2°, 17.1±0.2°, 18.2±0.2°, 19.4±0.2°, 20.0±0.2°, 20.3±0.2°, 20.9±0.2°, 22.6±0.2°, 24.9±0.2°, 25.2±0.2° and 25.9±0.2°.

In more preferred embodiments, the crystalline form II has an XRPD pattern comprising peaks at the following diffraction angles (2θ):

| Peak No. | 2θ(°) ± 0.2° | I % |
|---|---|---|
| 1 | 6.5 | 16.1 |
| 2 | 8.1 | 9.5 |
| 3 | 9.9 | 100 |
| 4 | 11.0 | 24.6 |
| 5 | 11.6 | 13.3 |
| 6 | 11.8 | 17.4 |
| 7 | 13.2 | 32.6 |
| 8 | 13.5 | 26.8 |
| 9 | 13.8 | 20 |
| 10 | 15.4 | 7.5 |
| 11 | 16.2 | 29.9 |
| 12 | 16.6 | 14 |
| 13 | 17.1 | 12.9 |
| 14 | 18.2 | 10.9 |
| 15 | 19.4 | 22.9 |
| 16 | 20.0 | 11.5 |
| 17 | 20.3 | 16.9 |
| 18 | 20.9 | 15.4 |
| 19 | 22.6 | 12.2 |
| 20 | 23.8 | 7 |
| 21 | 24.9 | 15.7 |
| 22 | 25.2 | 18.4 |
| 23 | 25.9 | 12.3 |
| 24 | 26.8 | 8.4 |
| 25 | 27.1 | 8.2 |
| 26 | 27.9 | 7 |
| 27 | 29.2 | 7.7 |
| 28 | 30.0 | 7 |
| 29 | 30.4 | 7.6 |
| 30 | 31.8 | 4.7 |
| 31 | 32.8 | 6.9 |
| 32 | 33.5 | 6.3 |
| 33 | 34.1 | 8.1 |
| 34 | 35.0 | 5.3 |
| 35 | 35.9 | 5.5 |
| 36 | 36.8 | 5 |
| 37 | 39.3 | 5.9 |
| 38 | | |
| 39 | | |

Figure 5:
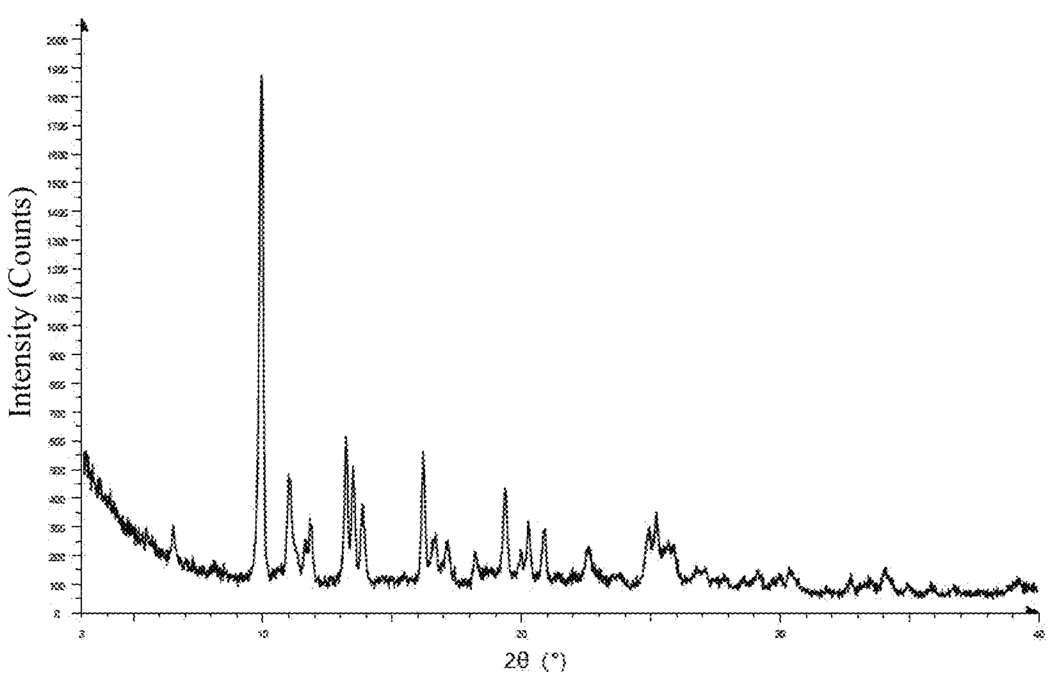
FIG. 5 is an XRPD pattern of crystalline form II of compound A monohydrochloride dihydrate.

In more preferred embodiments, the crystalline form II has an XRPD pattern comprising peaks at diffraction angles (2θ) essentially the same as shown in FIG. 5. In the most preferred embodiment, the XRPD pattern of crystalline form II is essentially the same as shown in FIG. 5.

In more preferred embodiments, the crystalline form II has a DSC graph comprising a broad endothermic peak at about 25-180° C. and an endothermic peak at about 217-243° C.

In more preferred embodiments, in a thermogravimetric analysis, the crystalline form II has a weight loss of about 7.1% when heated to about 180° C.

The DSC graph of the crystalline form II has a broad endothermic peak at 25-180° C., and the corresponding TGA graph shows a weight loss of about 7.1% before 180° C., indicating that the crystalline form II begins to lose water when the temperature is higher than 25° C.

Figure 6:
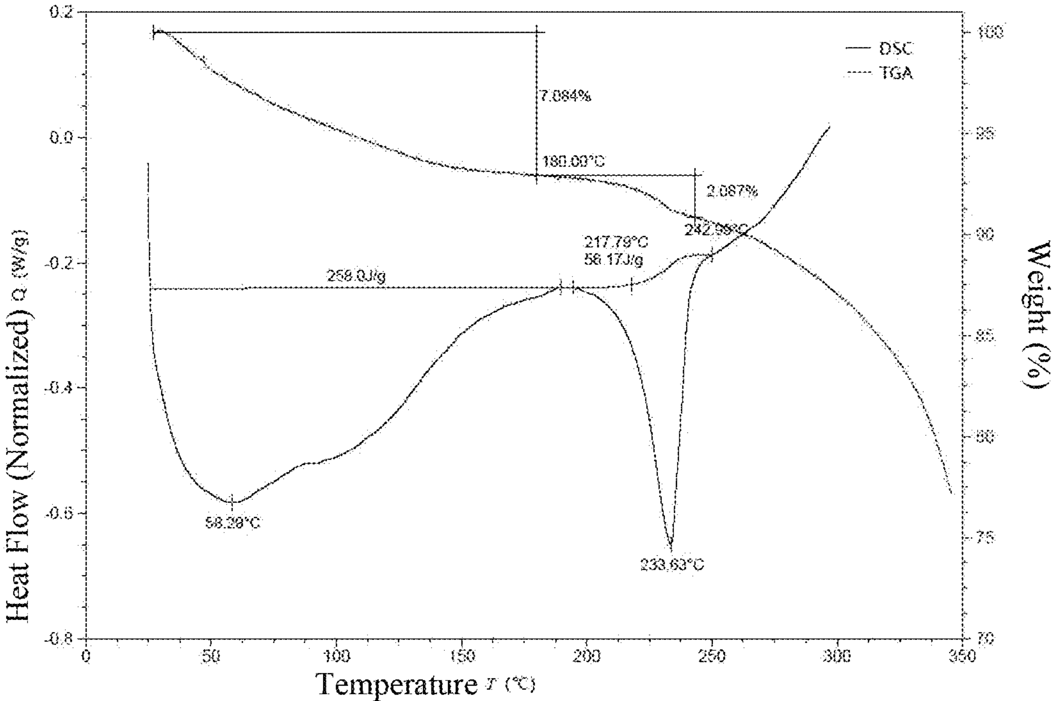
FIG. 6 is a DSC-TGA graph of crystalline form II of compound A monohydrochloride dihydrate.

In the most preferred embodiment, the crystalline form II has a DSC-TGA graph essentially the same as shown in FIG. 6.

Figure 7:
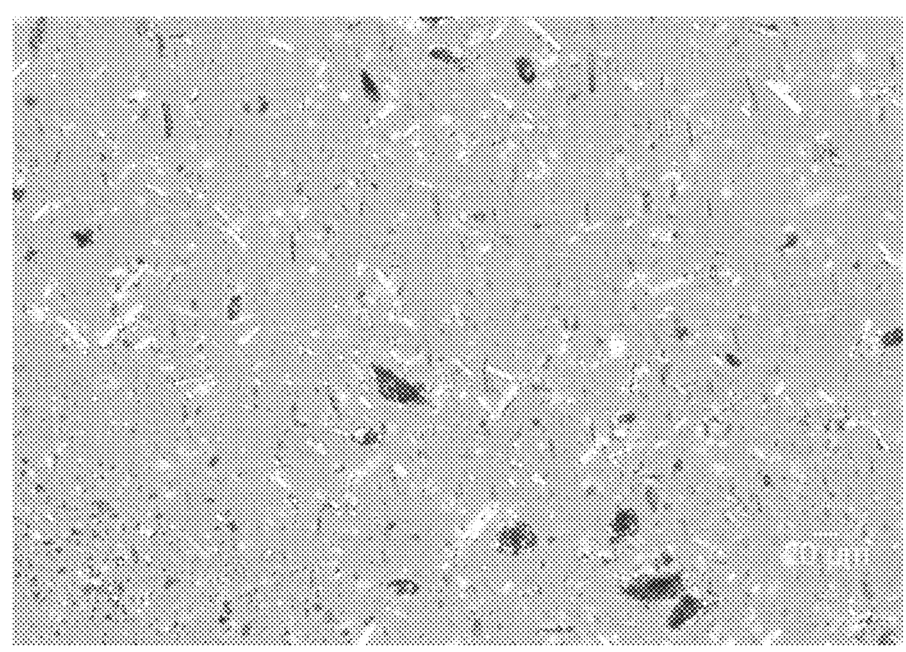
FIG. 7 is a scanning electron microscope image of crystalline form II of compound A monohydrochloride dihydrate.

In the most preferred embodiment, the crystalline form II has a scanning electron microscope image essentially the same as shown in FIG. 7.

In some embodiments, the present invention provides a method for preparing the crystalline form II of compound A monohydrochloride dihydrate, comprising adding the crystalline form I of compound A monohydrochloride monohydrate to an aqueous alcoholic solvent having 1-10 carbon atoms (the alcoholic solvent is preferably an alcohol having 1-6 carbon atoms, including but not limited to methanol, ethanol, 1-propanol (n-propanol), 2-propanol (isopropanol), 1-butanol, 2-butanol and tert-butanol; the weight-to-volume ratio (g/mL) of the crystalline form I to the alcoholic solvent is about 1:(1-100), preferably 1:50), stirring the solution at a temperature of about 10-40° C. (e.g., about 20-30° C.) for about 10-60 hours (e.g., about 50 hours), filtering and optionally drying to obtain the crystalline form.

In preferred embodiments, the compound A hydrochloride is crystalline form III of compound A monohydrochloride sesquihydrate;

the crystalline form III has an XRPD pattern comprising characteristic peaks at diffraction angles (2θ) of about 5.1±0.2°, 9.1±0.2° and 10.2±0.2°;

preferably comprising characteristic peaks at diffraction angles (2θ) of about 5.1±0.2°, 5.4±0.2°, 6.0±0.2°, 9.1±0.2°, 10.2±0.2°, 11.2±0.2° and 18.0±0.2°;

most preferably comprising characteristic peaks at diffraction angles (2θ) of about 5.1±0.2°, 5.4±0.2°, 6.0±0.2°, 6.3±0.2°, 7.5±0.2°, 7.8±0.2°, 8.4±0.2°, 9.1±0.2°, 10.2±0.2°, 10.7±0.2°, 11.2±0.2°, 12.2±0.2°, 12.5±0.2°, 12.9±0.2°, 13.7±0.2°, 13.9±0.2°, 15.4±0.2°, 15.7±0.2°, 16.2±0.2°, 16.8±0.2°, 18.0±0.2°, 18.7±0.2°, 19.3±0.2°, 20.0±0.2°, 20.6±0.2°, 21.5±0.2° and 23.3±0.2°.

In more preferred embodiments, the crystalline form III has an XRPD pattern comprising peaks at the following diffraction angles (2θ):

| Peak No. | 2θ(°) ± 0.2° | I % |
|---|---|---|
| 1 | 5.1 | 100 |
| 2 | 5.4 | 34.8 |
| 3 | 6.0 | 36 |
| 4 | 6.3 | 26.5 |
| 5 | 7.5 | 18.8 |
| 6 | 7.8 | 30.1 |
| 7 | 8.4 | 19.7 |
| 8 | 9.1 | 90.7 |
| 9 | 10.2 | 59 |
| 10 | 10.7 | 26.8 |
| 11 | 11.2 | 40.3 |
| 12 | 12.2 | 23.2 |
| 13 | 12.5 | 28.5 |
| 14 | 12.9 | 26 |
| 15 | 13.7 | 18.8 |
| 16 | 13.9 | 19.8 |
| 17 | 15.4 | 15.5 |

-continued

| Peak No. | 2θ(°) ± 0.2° | I % |
|---|---|---|
| 18 | 15.7 | 17.2 |
| 19 | 16.2 | 13.9 |
| 20 | 16.8 | 14.1 |
| 21 | 18.0 | 52.7 |
| 22 | 18.7 | 16.6 |
| 23 | 19.3 | 19.7 |
| 24 | 20.0 | 20.9 |
| 25 | 20.6 | 11.2 |
| 26 | 21.5 | 13.5 |
| 27 | 23.3 | 21.7 |
| 28 | 24.6 | 8.9 |
| 29 | 25.2 | 9.1 |
| 30 | 26.1 | 7.9 |
| 31 | 27.8 | 8.5 |
| 32 | 31.0 | 7 |

Figure 8:
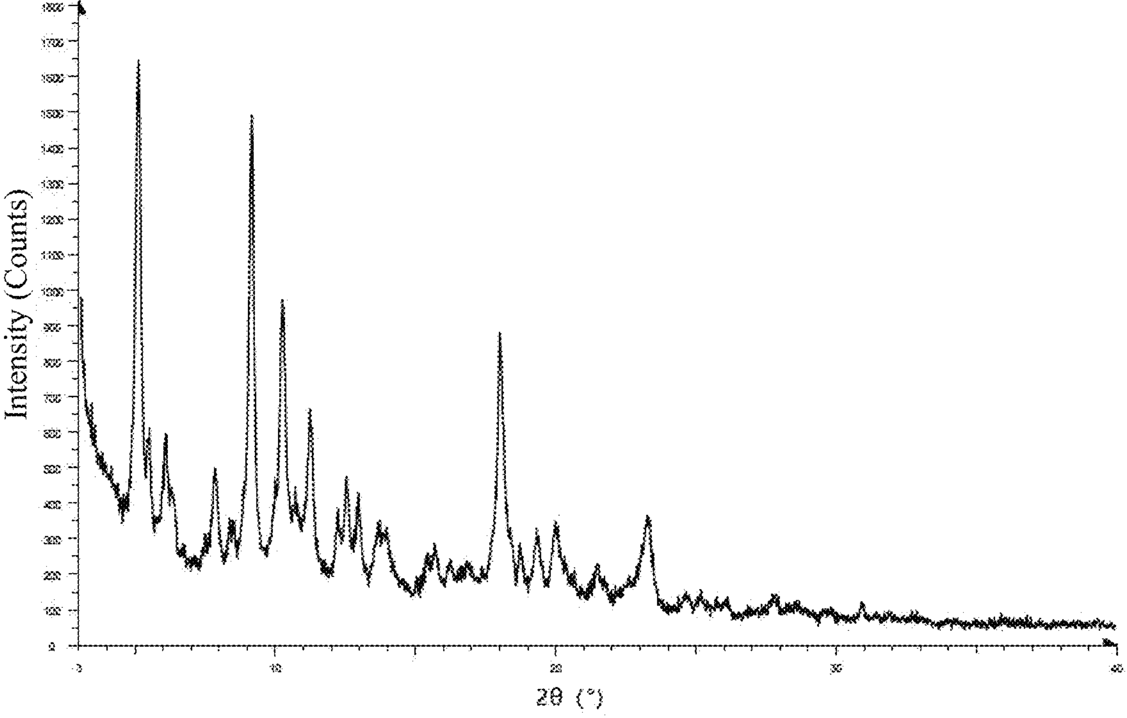
FIG. 8 is an XRPD pattern of crystalline form III of compound A monohydrochloride sesquihydrate.

In more preferred embodiments, the crystalline form III has an XRPD pattern comprising peaks at diffraction angles (2θ) essentially the same as shown in FIG. 8. In the most preferred embodiment, the XRPD pattern of crystalline form III is essentially the same as shown in FIG. 8.

In more preferred embodiments, the crystalline form III has a DSC graph comprising a broad endothermic peak at about 25-134° C. and endothermic peaks at about 137° C. and about 251° C.

In more preferred embodiments, in a thermogravimetric analysis, the crystalline form III has a weight loss of about 4.3% when heated to about 180° C.

The DSC graph of the crystalline form III has a broad endothermic peak and a small endothermic peak at 25-180° C., and the corresponding TGA graph shows a weight loss of about 4.3% before 180° C., indicating that the crystalline form III begins to lose water when the temperature is higher than 25° C.

Figure 9:
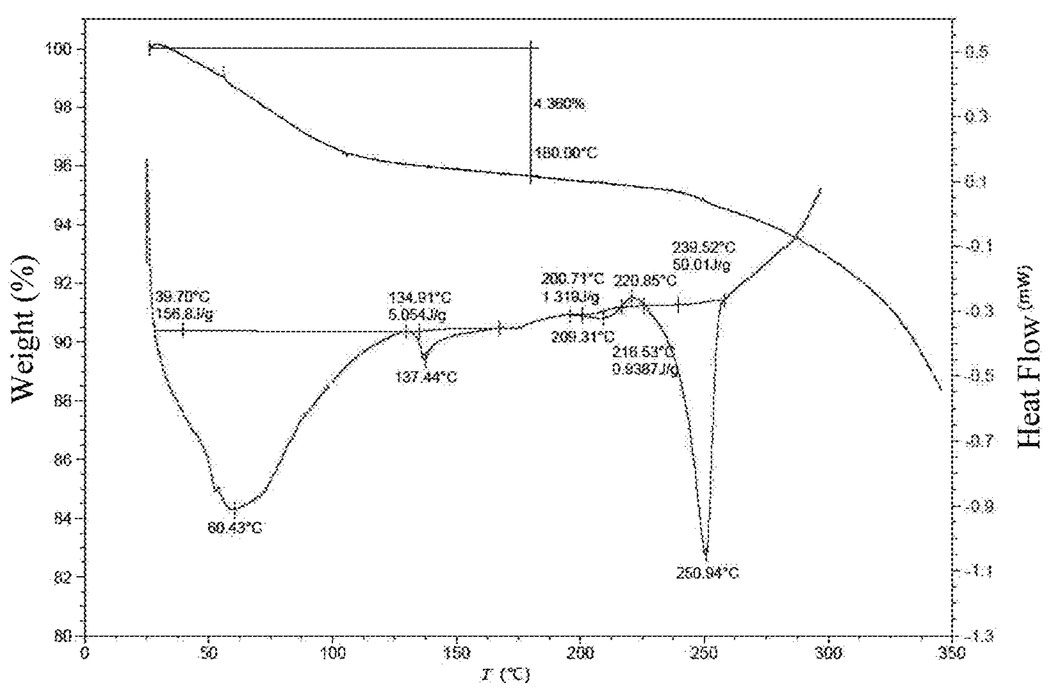
FIG. 9 is a DSC-TGA pattern of crystalline form III of compound A monohydrochloride sesquihydrate.

In the most preferred embodiment, the crystalline form III has a DSC-TGA graph essentially the same as shown in FIG. 9.

Figure 10:
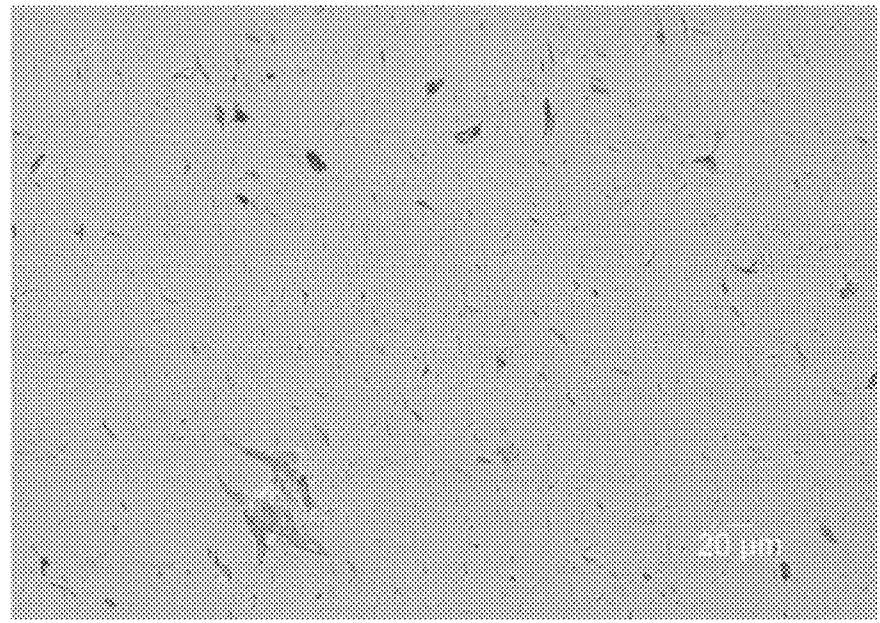
FIG. 10 is a scanning electron microscope image of crystalline form III of compound A monohydrochloride sesquihydrate.

In the most preferred embodiment, the crystalline form III has a scanning electron microscope image essentially the same as shown in FIG. 10.

In some embodiments, the present invention provides a method for preparing the crystalline form III of compound A monohydrochloride sesquihydrate, comprising adding the crystalline form I of compound A monohydrochloride monohydrate to an aqueous alcoholic solvent having 1-10 carbon atoms (the alcoholic solvent is preferably an alcohol having 1-6 carbon atoms, including but not limited to methanol, ethanol, 1-propanol (n-propanol), 2-propanol (isopropanol), 1-butanol, 2-butanol and tert-butanol; the weight-to-volume ratio (g/mL) of the crystalline form I to the alcoholic solvent is about 1:(1-100), preferably 1:50), adding an aromatic hydrocarbon solvent having 6-10 carbon atoms (e.g., toluene; the volume ratio of the alcoholic solvent to the aromatic hydrocarbon solvent is preferably about 1:(1-15), e.g., about 1:5) at a temperature of about 10-40° C. (e.g., about 20-30° C.), stirring the solution for about 1-6 hours (e.g., about 2 hours), filtering and optionally drying to obtain the crystalline form.

In preferred embodiments, the compound A hydrochloride is crystalline form IV of compound A monohydrochloride mono-dimethyl sulfoxide complex;

the crystalline form IV has an XRPD pattern comprising characteristic peaks at diffraction angles (2θ) of about 6.6±0.2°, 8.9±0.2° and 18.5±0.2°;

preferably comprising characteristic peaks at diffraction angles (2θ) of about 6.6±0.2°, 8.9±0.2°, 11.6±0.2°, 14.6±0.2°, 17.7±0.2°, 18.5±0.2°, 24.7±0.2° and 25.0±0.2°;

most preferably comprising characteristic peaks at diffraction angles (2θ) of about 4.1±0.2°, 6.6±0.2°, 8.9±0.2°, 11.2±0.2°, 11.6±0.2°, 13.3±0.2°, 13.8±0.2°, 14.6±0.2°, 15.7±0.2°, 17.7±0.2°, 18.1±0.2°, 18.5±0.2°, 19.4±0.2°, 20.0±0.2°, 20.7±0.2°, 21.4±0.2°, 22.0±0.2°, 22.6±0.2°, 23.0±0.2°, 23.8±0.2°, 24.7±0.2°, 25.0±0.2°, 26.5±0.2°, 27.9±0.2°, 29.7±0.2° and 32.8±0.2°.

In more preferred embodiments, the crystalline form IV has an XRPD pattern comprising peaks at the following diffraction angles (2θ):

| Peak No. | 2θ(°) ± 0.2° | I % |
|---|---|---|
| 1 | 4.1 | 26.8 |
| 2 | 6.6 | 64.5 |
| 3 | 8.9 | 71.3 |
| 4 | 11.2 | 18.4 |
| 5 | 11.6 | 55.5 |
| 6 | 13.3 | 18.4 |
| 7 | 13.8 | 19.4 |
| 8 | 14.6 | 39.4 |
| 9 | 15.7 | 21 |
| 10 | 17.7 | 54.3 |
| 11 | 18.1 | 28.6 |
| 12 | 18.5 | 100 |
| 13 | 19.4 | 23.6 |
| 14 | 20.0 | 26.2 |
| 15 | 20.7 | 27.8 |
| 16 | 21.4 | 21.1 |
| 17 | 22.0 | 24.8 |
| 18 | 22.6 | 26.5 |
| 19 | 23.0 | 22.9 |
| 20 | 23.8 | 18.1 |
| 21 | 24.7 | 38.1 |
| 22 | 25.0 | 38.6 |
| 23 | 26.5 | 17.9 |
| 24 | 27.9 | 21.6 |
| 25 | 29.7 | 16.8 |
| 26 | 32.8 | 10.9 |

Figure 11:
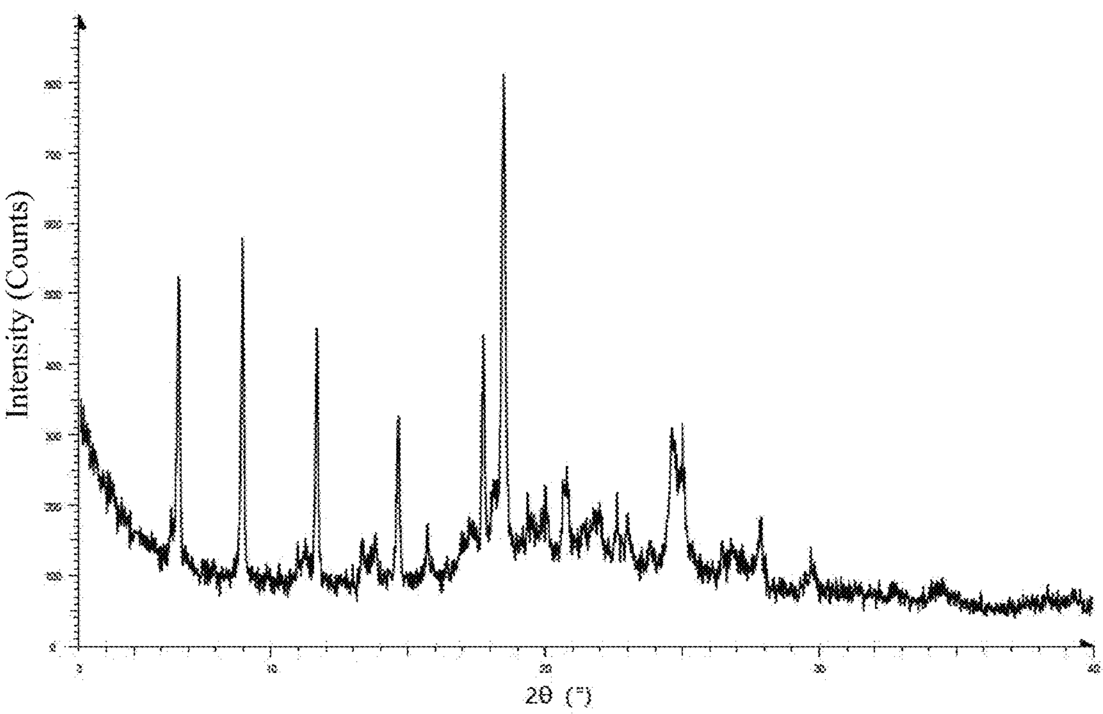
FIG. 11 is an XRPD pattern of crystalline form IV of compound A monohydrochloride mono-dimethyl sulfoxide complex.

In more preferred embodiments, the crystalline form IV has an XRPD pattern comprising peaks at diffraction angles (2θ) essentially the same as shown in FIG. 11. In the most preferred embodiment, the XRPD pattern of crystalline form IV is essentially the same as shown in FIG. 11.

In more preferred embodiments, the crystalline form IV has a DSC graph comprising endothermic peaks at about 47° C., about 93° C. and about 210° C.

Figure 12:
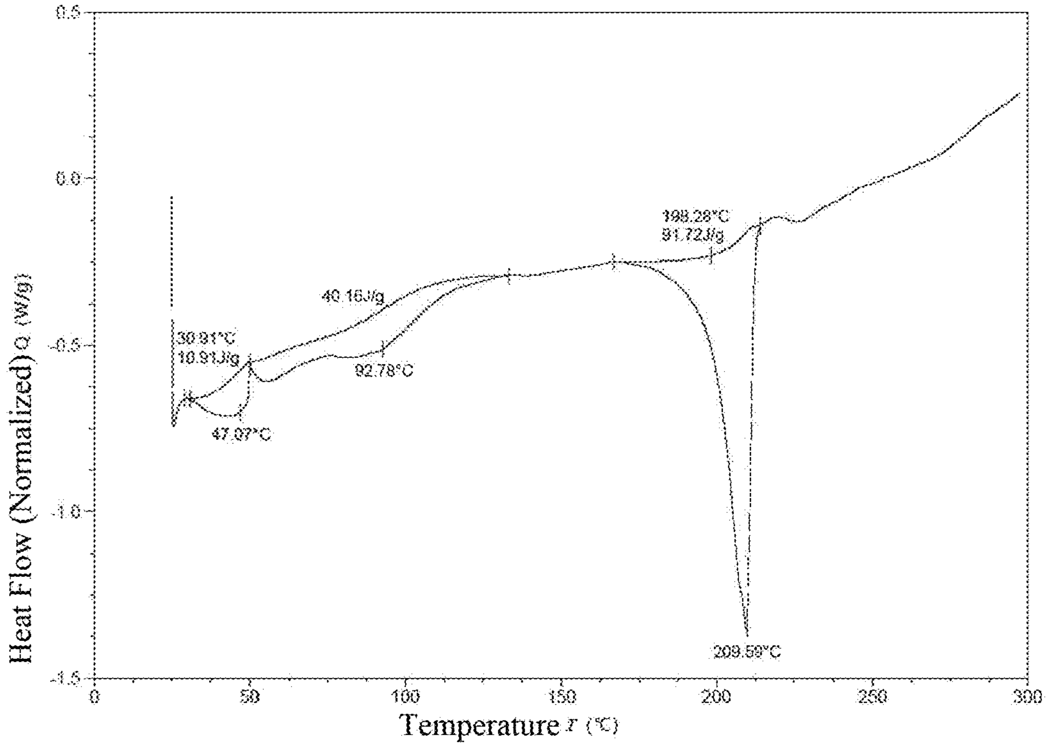
FIG. 12 is a DSC graph of crystalline form IV of compound A monohydrochloride mono-dimethyl sulfoxide complex.

In more preferred embodiments, the crystalline form IV has a DSC graph comprising characteristic peaks essentially the same as shown in FIG. 12. In the most preferred embodiment, the crystalline form IV has a DSC graph essentially the same as shown in FIG. 12.

In more preferred embodiments, in a thermogravimetric analysis, the crystalline form IV has a weight loss of about 14.1% when heated to about 217° C.

The DSC graph of the crystalline form IV has an endothermic peak at 30-217° C., and the corresponding TGA graph shows a weight loss of about 14.1% before 217° C., indicating that the crystalline form IV begins to lose the solvent (DMSO) when the temperature is higher than 30° C.

Figure 13:
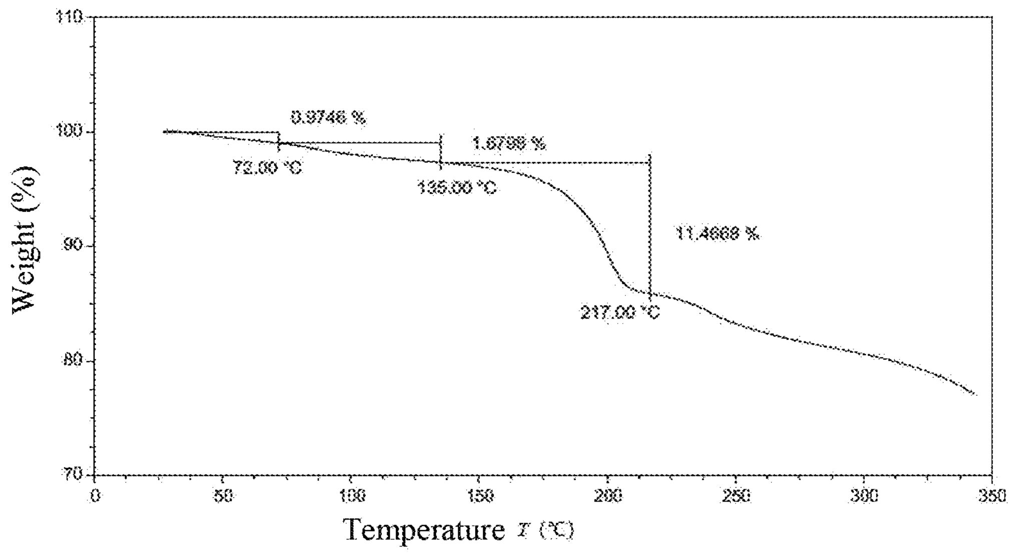
FIG. 13 is a TGA graph of crystalline form IV of compound A monohydrochloride mono-dimethyl sulfoxide complex.

In the most preferred embodiment, the crystalline form IV has a TGA graph essentially the same as shown in FIG. 13.

Figure 14:
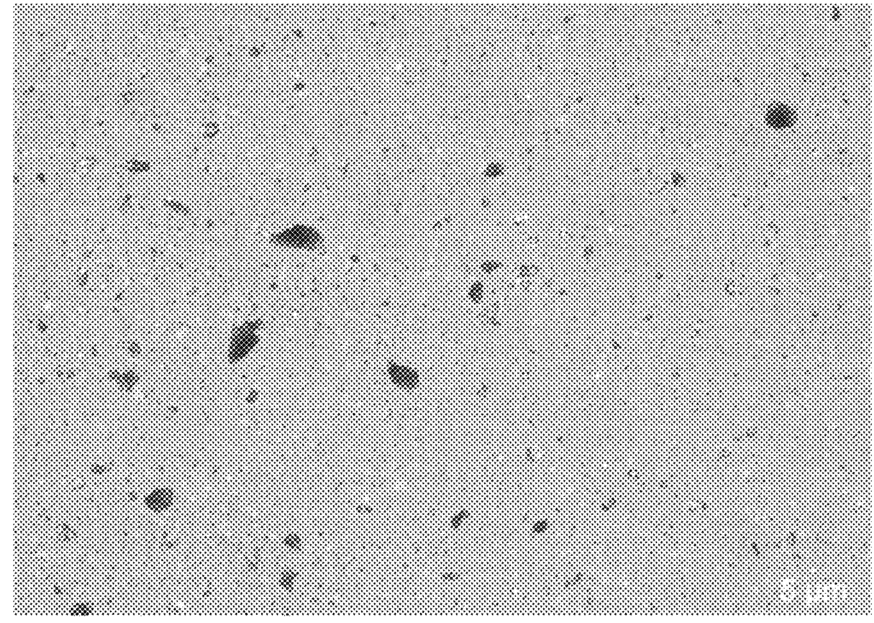
FIG. 14 is a scanning electron microscope image of crystalline form IV of compound A monohydrochloride mono-dimethyl sulfoxide complex.

In the most preferred embodiment, the crystalline form IV has a scanning electron microscope image essentially the same as shown in FIG. 14.

In some embodiments, the present invention provides a method for preparing crystalline form IV of compound A monohydrochloride mono-dimethyl sulfoxide complex, comprising adding the crystalline form I of compound A monohydrochloride monohydrate to dimethyl sulfoxide (the weight-to-volume ratio (g/mL) of the crystalline form I to the dimethyl sulfoxide is about 1:(1-100), preferably about 1:50), adding an aromatic hydrocarbon solvent having 6-10 carbon atoms (e.g., toluene; the volume ratio of the dimethyl sulfoxide to the aromatic hydrocarbon solvent is preferably about 1:(1-15), e.g., about 1:9) at a temperature of about 10-40° C. (e.g., about 20-30° C.), stirring the solution for about 1-6 hours (e.g., about 2 hours), filtering and optionally drying to obtain the crystalline form.

Pharmaceutical Composition, Therapeutic Method and Use Thereof

In some embodiments, the present invention provides a pharmaceutical composition comprising any one or more of the salt of compound A, and its crystalline forms I, II, III and IV of the present invention, and one or more pharmaceutically acceptable carriers.

In some embodiments, the present invention provides use of any one or more of the salt of compound A, and its crystalline forms I, II, III and IV of the present invention in the manufacture of a medicament as a Rho-associated protein kinase (ROCK) inhibitor, preferably selective ROCK2 inhibitor.

In some embodiments, the present invention provides any one or more of the salt of compound A, and its crystalline forms I, II, III and IV of the present invention for use as a Rho-associated protein kinase (ROCK) inhibitor, preferably selective ROCK2 inhibitor.

In some embodiments, the present invention provides a method for the prophylaxis or treatment of a disease mediated by the Rho-associated protein kinase (ROCK), comprising administering to a subject in need thereof, preferably a mammal, a prophylactically or therapeutically effective amount of any one or more of the salt of compound A, and its crystalline forms I, II, III and IV of the present invention.

In some embodiments, the disease mediated by the Rho-associated protein kinase (ROCK) includes an autoimmune disorder (comprising rheumatoid arthritis, systemic lupus erythematosus (SLE; lupus), psoriasis, Crohn's disease, atopic dermatitis, eczema, or graft-versus-host disease (GVHD)); a cardiovascular disorder (comprising hypertension, atherosclerosis, restenosis, cardiac hypertrophy, cerebral ischemia, cerebral vasospasm, or erectile dysfunction); inflammation (comprising asthma, cardiovascular inflammation, ulcerative colitis, or renal inflammation); a central nervous system disorder (comprising neuronal degeneration or spinal cord injury; and the central nervous system disorder is preferably Huntington's disease, Parkinson's disease, Alzheimer's disease, Amyotrophic lateral sclerosis (ALS), or multiple sclerosis); an arterial thrombotic disorder (comprising platelet aggregation, or leukocyte aggregation); a fibrotic disorder (comprising liver fibrosis, lung fibrosis, or kidney fibrosis); a neoplastic disease (comprising a lymphoma, carcinoma (e.g., squamous cell cancer, small-cell lung cancer, pituitary cancer, esophageal cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, bladder cancer, liver cancer, breast cancer, colon cancer, colorectal cancer, endometrial or uterine carcinoma, salivary gland carcinoma, kidney cancer, prostate cancer, vulval cancer, thyroid cancer, brain cancer, endometrial cancer, testis cancer, cholangiocarcinoma, gallbladder carcinoma, gastric cancer, melanoma, or head and neck cancer), leukemia, astrocytoma, soft tissue sarcoma, sarcoma, or blastoma); a metabolic syndrome; insulin resistance; hyperinsulinemia; type 2 diabetes; glucose intolerance; osteoporosis; an ocular disorder (comprising ocular hypertension, age related macular degeneration (AMD), choroidal neovascularization (CNV), diabetic macular edema (DME), iris neovascularization, uveitis, glaucoma (comprising primary open-angle glaucoma, acute angle-closure glaucoma, pigmentary glaucoma, congenital glaucoma, normal tension glaucoma, secondary glaucoma or neo vascular glaucoma), or retinitis of prematurity (ROP)).

In some embodiments, the disease mediated by the Rho-associated protein kinase (ROCK) includes lupus nephritis, atherosclerosis, rheumatoid arthritis (RA), hemangioma, angiofibroma, lung fibrosis, psoriasis, corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis, delayed hypersensitivity, inflammatory bowel disease, septic shock, osteoporosis, osteoarthritis, neuronal inflammation, Osier-Weber syndrome, restenosis, fungal infection, parasitic infection, and viral infection.

As used herein, the term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g., Remington's Pharmaceutical Sciences (1990).

The composition of the present invention can act systemically and/or topically. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the composition of the present invention can be administered in a suitable dosage form.

The dosage form may be solid, semi-solid, liquid, or gas formulations, specifically including, but not limited to, tablets, capsules, powders, granules, lozenges, hard candies, powders, sprays, creams, salves, suppositories, gels, pastes, lotions, ointments, aqueous suspensions, injectable solutions, suspensions, elixirs, and syrups.

The pharmaceutical composition of the present invention may be manufactured by any process well known in the art, e.g., by means of mixing, dissolving, granulating, dragee-making, levigating, emulsifying, lyophilizing processes, or the like.

As used herein, the term "therapeutically effective amount" refers to the amount of the compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, and 25 mg, etc.

Unless otherwise indicated, the term "treating" or "treatment", as used herein, means reversing, alleviating, inhibiting the progress of, or preventing a disorder, condition, or disease to which such term applies, or one or more symptoms of such disorder, condition, or disease.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

EXAMPLE

The present invention is explained in more detail below with reference to the examples, which are only used to illustrate the technical solutions of the present invention, and are not intended to limit the scope thereof. Those skilled in the art may make some non-essential improvements and adjustments, which still fall within the scope of the present invention.

Unless otherwise specified, the starting materials and reagents employed in the following Examples are all commercially available products or can be prepared through known methods.

The detection instruments and conditions used in the following examples are as follows:

(1) X-ray powder diffraction (XRPD)

(a) Instrument Model: Bruker D8 advance, equipped with a LynxEye detector

Test conditions: the anode target material was copper, the light pipe was set to (40 KV 40 mA), the 2θ scan angle for the sample was from 3° to 40°, and scan step was 0.02°.

(b) Instrument Model: Bruker D2 phaser

Test conditions: the anode target material was copper, the light pipe was set to (30 KV 10 mA), the 2θ scan angle for the sample was from 4° to 50°, and scan step was 0.02°.

(2) differential scanning calorimetry analysis (DSC)

Instrument Model: (a) TA Discovery DSC 250 (TA Instruments, US); (b) TA Discovery DSC 25 (TA Instruments, US)

Test conditions: the heating rate was 10° C./min, and dry nitrogen was used as the purge gas.

(3) thermogravimetric analysis (TGA)

Instrument Model: (a) Discovery TGA 55 (TA Instruments, US); (b) TGA 4000 (PerkinElmer, Germany)

Test conditions: automatic weighing in the heating furnace, the heating rate was 10° C./min, and dry nitrogen was used as the purge gas.

(4) polarizing microscope analysis (PLM)

Instrument Model: Polarizing Microscope ECLIPSE LV100POL (Nikon, JPN)

(5) Nuclear magnetic resonance ($^1$H NMR)

Instrument Model: Bruker Advance 400, equipped with B-ACS 120 automatic sampling system (6) Dynamic vapour sorption analysis (DVS)

Instrument Model: DVS Intrinsic (SMS, UK)

Test conditions: a gradient mode was used, the humidity ranged from 0% to 90%, the humidity increment of each gradient was 10%, and the holding time of each gradient was 1 h.

Example 1: Preparation of (6-(4-((4-(1H-pyrazol-4-yl)phenyl)amino)pyrimidin-2-yl)-1-methyl-1H-indol-2-yl)(3,3-difluoroazetidin-1-yl)methanone (Compound A) (According to PCT/CN2018/093713, which is Incorporated Herein by Reference in its Entirety)

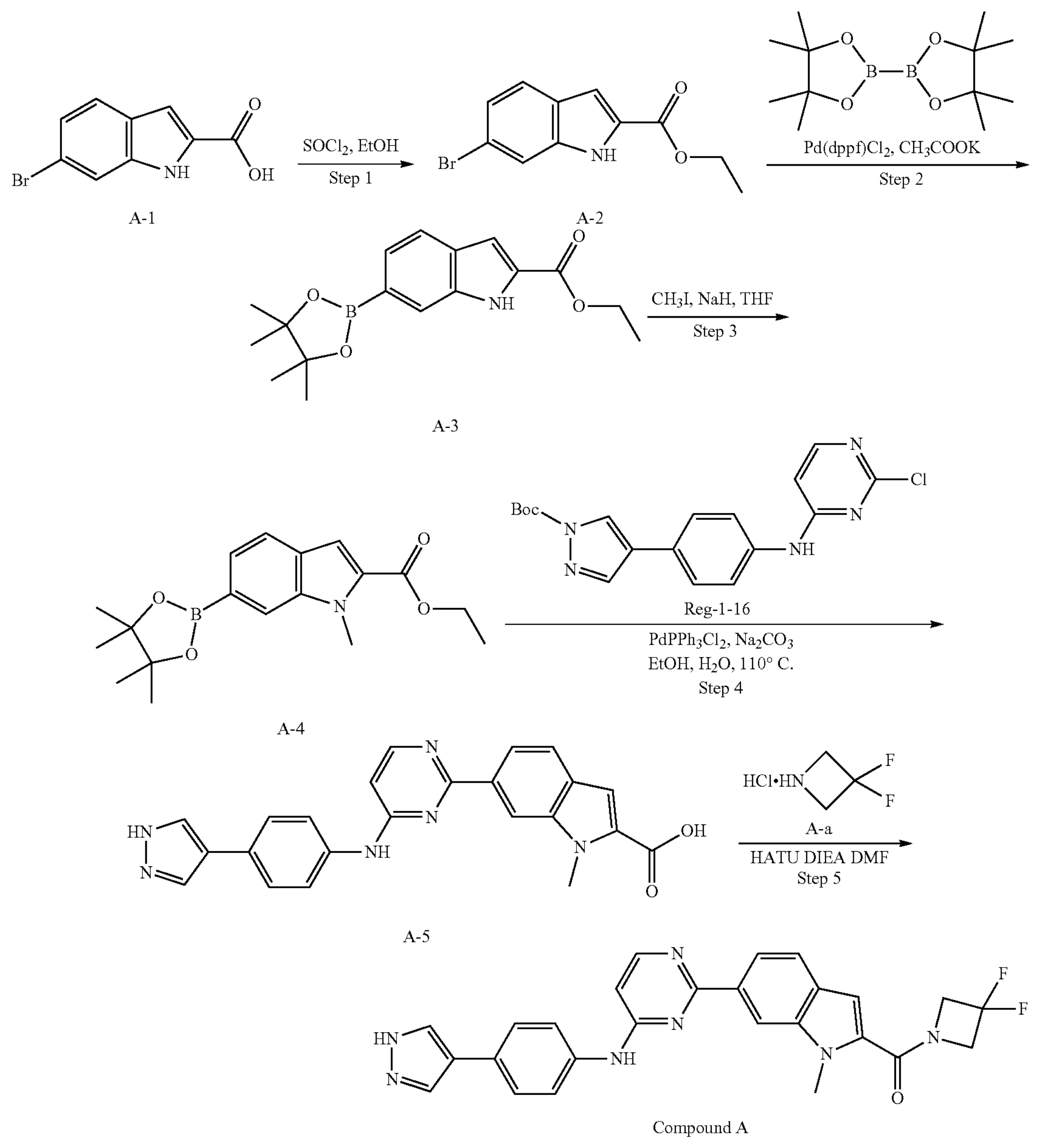

A-1

A-2

A-3

A-4

A-5

Compound A

Step 1:

Compound A-1 (20 g, 83.31 mmol) and ethanol (200 mL) were added to a 500 mL flask, thionyl chloride (19.82 g, 166.63 mmol) was added, and then the reaction was performed at 60° C. for 3 hours. Thin layer chromatography (petroleum ether/ethyl acetate=10:1) assay indicated the reaction was complete. The reaction solution was concentrated to afford a crude product, which was dissolved in dichloromethane (500 mL), and the resulting solution was washed twice with a saturated aqueous solution of sodium bicarbonate (150 mL each). The organic phase was washed with saturated brine, then dried over anhydrous sodium sulfate, filtered, and concentrated to afford compound A-2 (21 g, brown solid, yield: 94.01%). MS m/z (ESI): 266.1; 268.1 [M−H].

Step 2:

Compound A-2 (21 g, 78.33 mmol) and bis(pinacolato) diboron (26.85 g, 105.74 mmol) were dissolved in 1,4-dioxane (200 mL), potassium acetate (23.06 g, 234.98 mmol) and $Pd(dppf)Cl_2$ (3.24 g, 3.91 mmol) were added, purge with argon was performed for 3 times, and the reaction was placed in an oil bath at 80° C. overnight. LC-MS indicated the reaction was complete. The reaction solution was cooled to room temperature, concentrated under reduced pressure, and the residue was purified by column chromatography (petroleum ether/ethyl acetate=100:1 to 5:1) to afford compound A-3 (17.5 g, white solid, yield: 70.89%).

$^1$H NMR (400 MHz, $CDCl_3$) δ 8.92 (s, 1H), 7.92 (s, 1H), 7.69 (d, J=8.1 Hz, 1H), 7.57 (d, J=8.1 Hz, 1H), 7.22-7.18 (m, 1H), 4.42 (q, J=7.1 Hz, 2H), 1.42 (t, J=7.1 Hz, 3H), 1.37 (s, 12H). MS m/z (ESI): 316.2 [M+H].

Step 3:

Compound A-3 (10.0 g, 31.8 mmol) was dissolved in tetrahydrofuran (250 mL), sodium hydride (1.91 g, 47.8 mmol) was added under ice bath cooling, and then the reaction was performed for 30 minutes. Iodomethane (13.5 g, 95.4 mmol) was slowly added to the reaction solution, and the reaction was performed at room temperature overnight. Thin layer chromatography (petroleum ether/ethyl acetate=5:1) indicated the reaction was complete. The reaction solution was quenched with water (100 mL), and extracted with ethyl acetate (150 mL×2). The combined organic phases were washed sequentially with a saturated aqueous solution of ammonium chloride (200 mL×2) and saturated brine (300 mL×2), dried over anhydrous sodium sulfate, filtered, and concentrated. The crude product was separated and purified by column chromatography (petroleum ether/ethyl acetate=15:1) to afford compound A-4 (6.5 g, yellow solid, yield: 62.5%).

$^1$H NMR (400 MHz, $CDCl_3$) δ 7.91 (s, 1H), 7.68-7.65 (m, 1H), 7.57 (d, J=8.0 Hz, 1H), 7.27 (s, 1H), 4.12 (s, 3H), 3.91 (s, 3H), 1.38 (s, 12H).

Step 4:

Compound Reg-1-16 (1.00 g, 2.70 mmol) and A-4 (1.33 g, 4.04 mmol) were dissolved in a mixed solution of ethanol/water (8:1) (120 mL), sodium carbonate (572 mg, 5.40 mmol) and $Pd(PPh_3)Cl_2$ (189 mg, 0.27 mmol) were added, purge with argon was performed for 3 times, and the reaction was placed in an oil bath at 110° C. overnight. LC-MS indicated the reaction was complete. The reaction solution was cooled to room temperature, and concentrated under reduced pressure. The residue was diluted with water (30 mL), and the pH was adjusted to 1 with 6N HCl. A large amount of solid precipitated, and was filtered. The solid was washed with methanol to afford compound A-5 (900 mg, yellow solid, crude product).

$^1$H NMR (400 MHz, DMSO-$d_6$) δ 11.54 (s, 1H), 8.77 (s, 1H), 8.38 (d, J=7.2 Hz, 1H), 8.14 (s, 2H), 8.03 (d, J=8.8 Hz, 1H), 7.92 (d, J=8.4 Hz, 1H), 7.80-7.69 (m, 4H), 7.33 (s, 1H), 7.07 (d, J=8.0 Hz, 1H), 4.16 (s, 3H).

Step 5:

Compound A-5 (300 mg, 0.73 mmol) was dissolved in N,N-dimethylformamide (6 mL), HATU (335 mg, 0.88 mmol) and DIEA (377 mg, 2.92 mmol) were added, and the reaction was performed at room temperature for 30 min. Then, compound A-a (114 mg, 0.88 mmol) was added, and the reaction was continued at room temperature for 2 hours. LC-MS indicated the reaction was complete. The reaction solution was concentrated under reduced pressure, and the crude product was purified by high performance liquid chromatography to afford compound A (185 mg, yellow solid, yield: 52.1%).

$^1$H NMR (400 MHz, DMSO-$d_6$) δ 10.63 (s, 1H), 8.52 (s, 1H), 8.41 (d, J=6.4 Hz, 1H), 8.09 (s, 2H), 8.06 (dd, J=8.4, 1.2 Hz, 1H), 7.83 (d, J=8.4 Hz, 1H), 7.77 (d, J=8.0 Hz, 2H), 7.72 (d, J=8.4 Hz, 2H), 7.13 (s, 1H), 6.86 (d, J=6.4 Hz, 1H), 4.91 (s, 2H), 4.57 (s, 2H), 4.05 (s, 3H). MS m/z (ESI): 486.2 [M+H].

Example 2: Preparation of Crystalline Form I of Compound a Monohydrochloride Monohydrate Compound A (3.7 g) was added to a reaction flask, acetone (250 ml) was added, the reaction solution was heated to 50° C. and stirred for 10 min, the solid completely dissolved. Water (26.7 ml) was added, and the mixture was stirred to get a clear solution. Concentrated hydrochloric acid (12 mol/L) (0.641 ml) was added, and a large amount of solids precipitated. The mixture was stirred at 50° C. for 18 h, and filtered. The solid was collected, and dried under vacuum at 50° C. for 8 h to obtain a crystalline form (2.5 g, yield: 60.8%). The XRPD pattern obtained by X-ray powder diffraction analysis is shown in FIG. 1; upon DSC and TGA analysis, the DSC graph is shown in FIG. 2, and the TGA graph is shown in FIG. 3; the sample was examined through a scanning electron microscope, and the crystal morphology is shown in FIG. 4.

$^1$H NMR (400 MHz, DMSO-$d_6$) δ: 11.19 (s, 1H), 8.68 (s, 1H), 8.39 (d, J=6.8 Hz, 1H), 8.11 (s, 2H), 8.04 (d, J=8 Hz, 1H), 7.86 (d, J=8 Hz, 1H), 7.78-7.73 (m, 4H), 7.14 (s, 1H), 6.99 (d, J=6.4 Hz, 1H), 4.99-4.57 (brs, 4H), 4.07 (s, 3H).

Example 3: Preparation of Crystalline Form II of Compound a Monohydrochloride Dihydrate The crystalline form I of compound A monohydrochloride monohydrate (2.0 g) was added to methanol (100 ml, water content: 0.08%), the mixture was stirred at 20-30° C. for 48 h, and filtered to collect the solid, which was dried under vacuum at 50° C. for 8 h, to obtain a crystalline form (1.0 g, yield: 48.4%). The XRPD pattern obtained by X-ray powder diffraction analysis is shown in FIG. 5; the DSC-TGA graph obtained by the DSC and TGA analysis is shown in FIG. 6; the sample was examined through a scanning electron microscope, and the crystal morphology is shown in FIG. 7.

$^1$H NMR (400 MHz, DMSO-$d_6$) δ: 11.18 (s, 1H), 8.65 (s, 1H), 8.39 (d, J=6.8 Hz, 1H), 8.10 (s, 2H), 8.04 (d, J=8 Hz, 1H), 7.86 (d, J=8 Hz, 1H), 7.778-7.73 (m, 4H), 7.14 (s, 1H), 6.97 (d, J=6.4 Hz, 1H), 4.91-4.57 (brs, 4H), 4.06 (s, 3H).

Example 4: Preparation of Crystalline Form III of Compound A Monohydrochloride Sesquihydrate The crystalline form I of compound A monohydrochloride monohydrate (2.0 g) was added to methanol (100 ml, water content: 0.08%), the temperature was maintained at 20-30° C., toluene (560 ml) was added dropwise, and a solid precipitated. The mixture was stirred for 2 h, and filtered to collect the solid, which was dried under vacuum at 50° C. for 8 h, to obtain a crystalline form (1.1 g, yield: 54.2%). The XRPD pattern obtained by X-ray powder diffraction analysis is shown in FIG. 8; the DSC-TGA graph obtained by the DSC and TGA analysis is shown in FIG. 9; the sample was examined through a scanning electron microscope, and the crystal morphology is shown in FIG. 10.

$^1$H NMR (400 MHz, DMSO-$d_6$) δ: 10.98 (s, 1H), 8.61 (s, 1H), 8.37 (d, J=6.8 Hz, 1H), 8.10 (s, 2H), 8.04 (d, J=8 Hz, 1H), 7.85 (d, J=8 Hz, 1H), 7.77-7.72 (m, 4H), 7.13 (s, 1H), 6.94 (d, J=6.4 Hz, 1H), 4.91-4.57 (brs, 4H), 4.05 (s, 3H).

Example 5: Preparation of Crystalline Form IV of Compound A Monohydrochloride Mono-Dimethyl Sulfoxide Complex The crystalline form I of compound A monohydrochloride monohydrate (2.0 g) was added to dimethyl sulfoxide (100 ml), the temperature was maintained at 20-30° C., toluene (900 ml) was added dropwise, and a solid precipitated. The mixture was stirred for 2 h, and filtered to collect the solid, which was dried under vacuum at 50° C. for 8 h, to obtain a crystalline form (0.8 g, yield: 36.0%). The XRPD pattern obtained by X-ray powder diffraction analysis is shown in FIG. 11; upon DSC and TGA analysis, the DSC graph is shown in FIG. 12, and the TGA graph is shown in FIG. 13; the sample was examined through a scanning electron microscope, and the crystal morphology is shown in FIG. 14.

$^1$H NMR (400 MHz, DMSO-$d_6$) δ: 11.06 (s, 1H), 8.64 (s, 1H), 8.37 (d, J=6.8 Hz, 1H), 8.10 (s, 2H), 8.04 (d, J=8 Hz, 1H), 7.85 (d, J=8 Hz, 1H), 7.77-7.72 (m, 4H), 7.13 (s, 1H), 6.94 (d, J=6.4 Hz, 1H), 4.95-4.57 (brs, 4H), 4.06 (s, 3H), 2.36 (s, 6H).

EXPERIMENTAL EXAMPLE

Experimental Example 1: Pharmacokinetic Test

The crystalline form I of compound A monohydrochloride monohydrate and compound A (vehicles for both samples were 0.5% CMC-Na) were respectively orally administered once to two groups of beagle dogs at a dose of 20 mpk, and blood samples were collected before the administration (0 h) and at 0.25, 0.5, 1, 2, 4, 6, 8 and 24 hours after the administration. The samples were processed and subjected to a chromatographic analysis. The test results are shown in the table below:

| Drug | $C_{max}$ (ng/mL) | $AUC_{0\text{-}last}$ (ng · h/mL) |
|---|---|---|
| Crystalline form I of compound A monohydrochloride monohydrate | 3856.987 | 19433.501 |
| Compound A | 146.605 | 521.765 |

According to the above results, the exposure upon oral administration of crystalline form I of compound A monohydrochloride monohydrate is significantly better than that of compound A.

Experimental Example 2: Solid Stability Test

Figure 15:
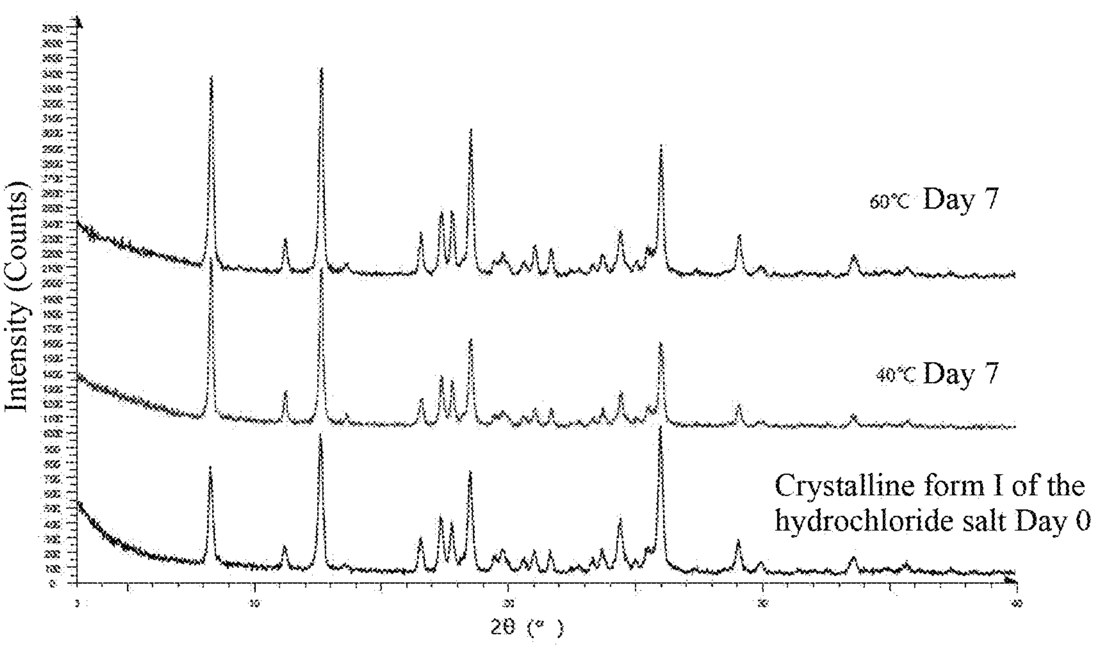
FIG. 15 is an XRPD pattern of the samples obtained in the solid stability test of Experimental Example 2.

Crystalline form I of compound A monohydrochloride monohydrate was placed under the conditions of 40° C./75% RH and 60° C./90% RH for 7 days, respectively, and was subjected to X-ray powder diffraction analysis. The test results are shown in FIG. 15. The results showed that the crystalline form I of compound A monohydrochloride monohydrate did not change.

Experimental Example 3: Solubility Test

Crystalline form I of compound A monohydrochloride monohydrate was tested for solubility in a simulated gastric fluid (SGF), fed state simulated intestinal fluid (FeSSIF), and fasted state simulated intestinal fluid (FaSSIF), respectively. The test results are as follows:

SGF: 0.0012 mg/ml;
FeSSIF: 0.017 mg/ml;
FaSSIF: 0.00028 mg/ml.

Experimental Example 4: DVS Test

Figure 16:
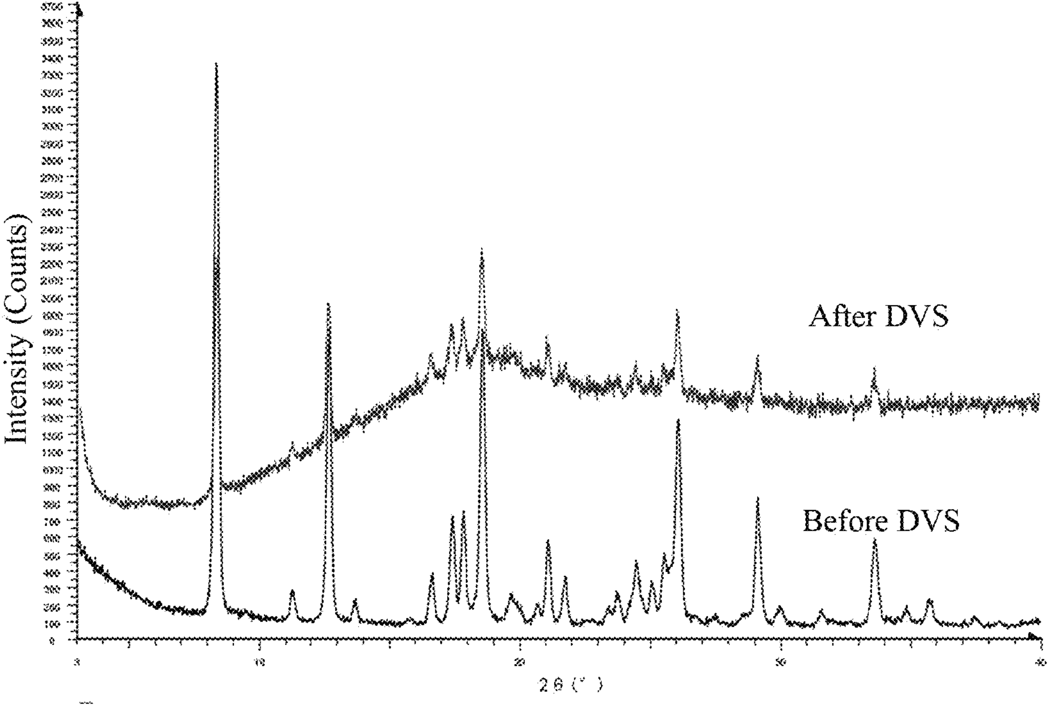
FIG. 16 is an XRPD pattern of the samples before and after the DVS test of Experimental Example 4.

The dynamic moisture adsorption-desorption curve of the crystalline form I of compound A monohydrochloride monohydrate was determined using DVS Intrinsic (SMS, UK) in a gradient mode with a humidity range of 0% to 90% (the humidity increment was 10% for each gradient, and each gradient was maintained for 1 h), and the crystalline form of the sample before and after the DVS test was tested by XRPD. DVS indicated that the crystalline form I of compound A monohydrochloride monohydrate had a water absorption of 0.67% at 0-10% RH, and a water absorption of 0.9% at 10-90% RH; the XRPD patterns of the sample before and after the DVS test are shown in FIG. 16. According to FIG. 16, the crystalline form I of compound A monohydrochloride monohydrate did not change after the DVS test.

Experimental Example 5: Crystalline Form Transformation Test

Figure 17:
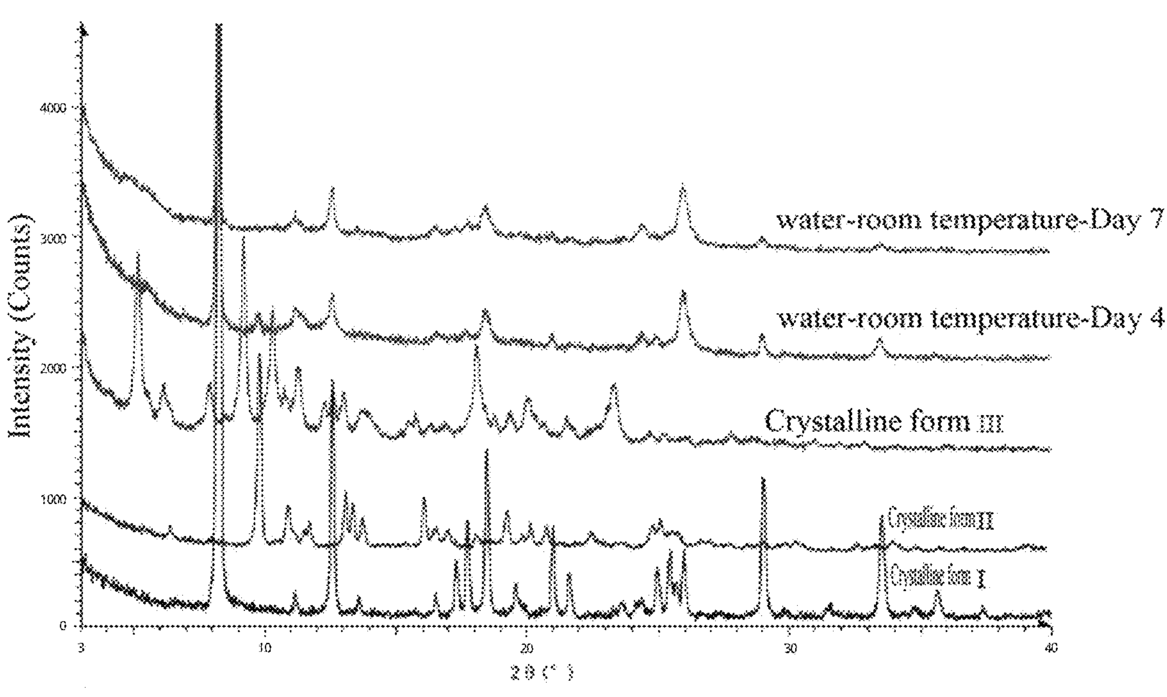
FIG. 17 is an XRPD pattern of the samples before and after the crystalline form transformation test in water of Experimental Example 5.

About 5 mg of each of crystalline form I, crystalline form II and crystalline form III were mixed and placed in a 4 mL vial, and then 0.8 mL of water was added. The suspension was stirred at room temperature for 7 days. The mixture was subjected to X-ray powder diffraction analysis on Day 4 and Day 7, and the results are shown in FIG. 17. The results showed that on Day 4, the mixture transformed as a mixed crystal of crystalline form I and crystalline form II, and crystalline form III disappeared; on Day 7, the mixture completely transformed as crystalline form I. This indicates that the most stable crystalline form in water at room temperature is crystalline form I.

Experimental Example 6: Grinding Test

Figure 18:
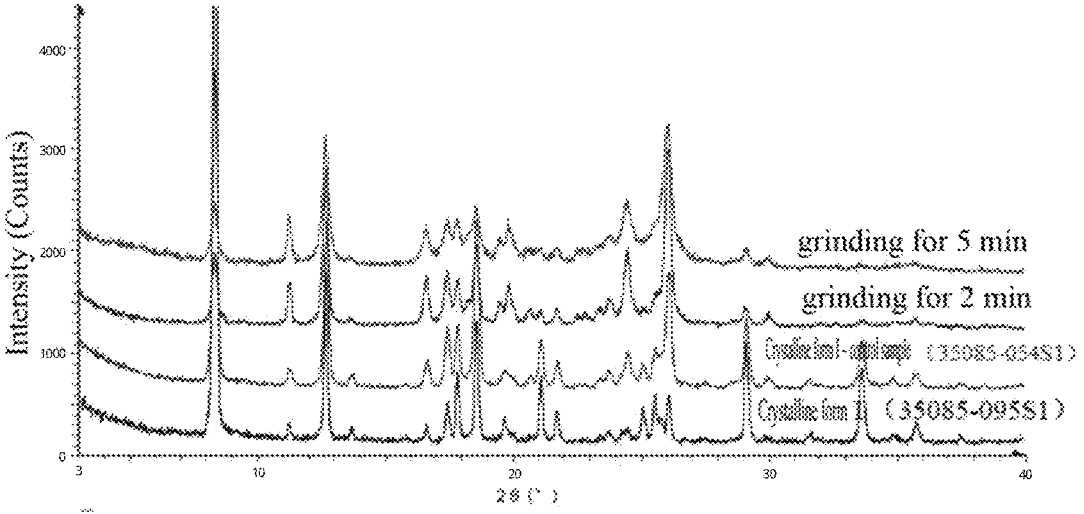
FIG. 18 is an XRPD pattern of the samples obtained in the grinding test of Experimental Example 6.

An appropriate amount of crystalline form I of compound A monohydrochloride monohydrate was taken and ground for 2 minutes and 5 minutes, respectively, and subjected to an X-ray powder diffraction analysis. The test results are shown in FIG. 18. The results indicates that the crystalline form did not change.

Experimental Example 7: Solid Stability Test 20.8 mg of crystalline form I of compound A monohydrochloride monohydrate was taken and placed in a 4 mL vial. The vial was left open, and dried under vacuum at 50° C. for 2 days. The sample was subjected to X-ray powder diffraction and TGA analyses, and the results are shown in FIG. 19 and FIG. 20.

19.3 mg of crystalline form I of compound A monohydrochloride monohydrate was taken and placed in a 4 mL vial. The vial was left open, and placed under a condition of 25° C./92.5% RH for 7 days. The sample was subjected to X-ray powder diffraction analysis, and the results are shown in FIG. 19.

Figure 19:
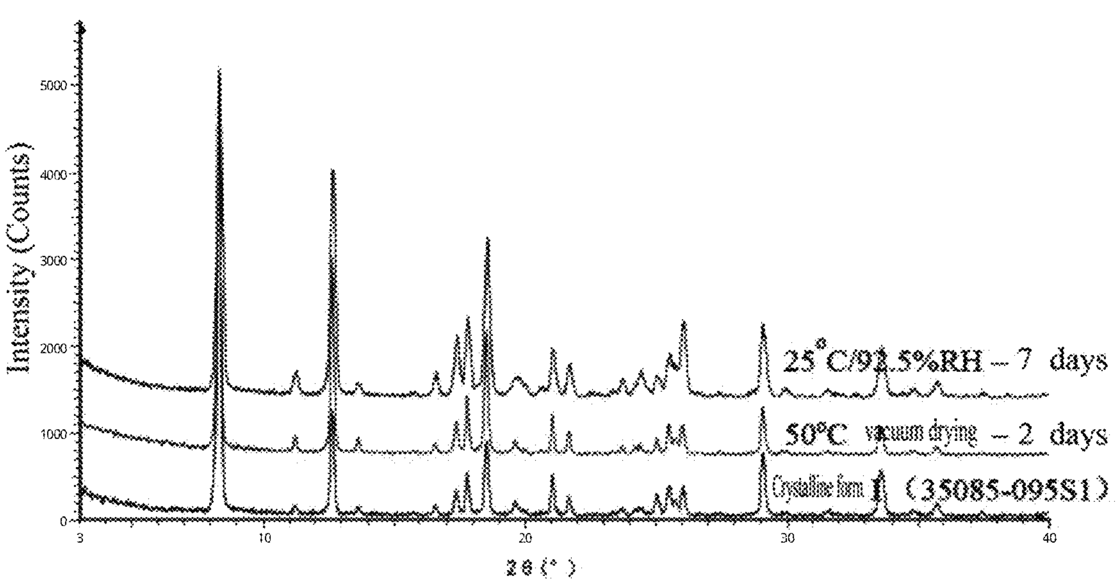
FIG. 19 is an XRPD spectrum of the samples obtained in the solid stability test of Experimental Example 7.
Figure 20:
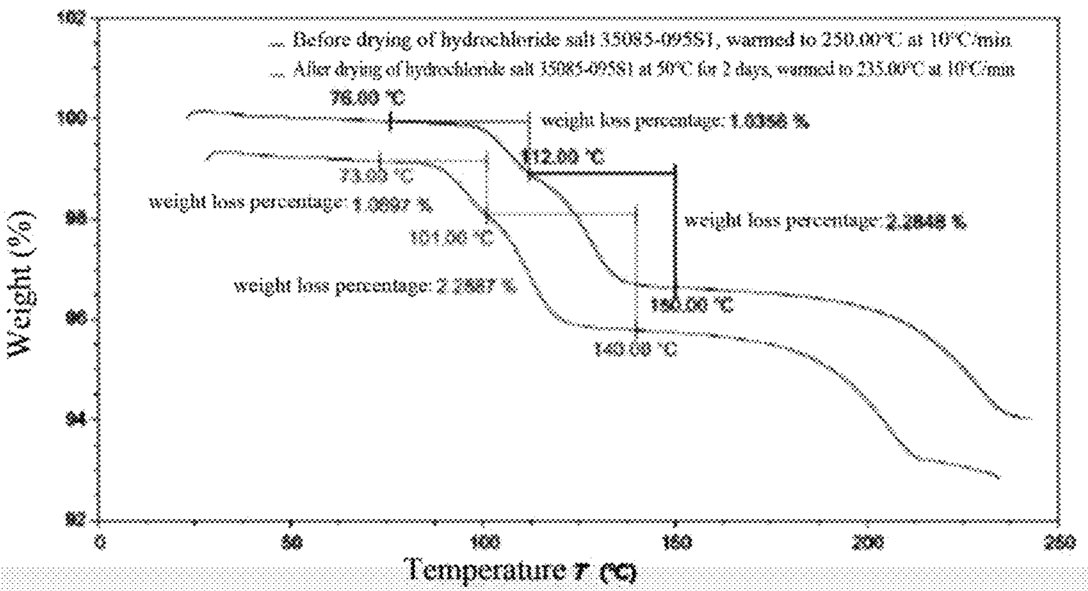
FIG. 20 is a TGA graph of the samples obtained in the solid stability test of Experimental Example 7.

Results in FIG. 19 and FIG. 20 indicated that the physical stability of crystalline form I of compound A monohydrochloride monohydrate was good, and the crystalline form did not change. The TGA weight loss of the sample after drying did not change, indicating that the water molecules and the drug molecules are firmly associated in crystalline form I.

Experimental Example 8: Determination of the Chloride Ion Content in the Sample by Potentiometric Titration 270 mg of crystalline form I of compound A monohydrochloride monohydrate was taken and placed in a titration beaker, 25 mL of dimethyl sulfoxide was firstly added to dissolve, then 15 mL of water was added, and the solution was stirred thoroughly. The titration was performed by Mettler T50 potentiometric titrator with DMI141-SC silver electrode and silver nitrate titration solution (0.1 mol/L), and the chloride ion content in the sample was calculated according to the consumption of the silver nitrate titration solution. The chloride ion content in multiple batches of the samples as determined by this method was between 6.5% and 6.7%, while the theoretical content of chloride ion in compound A monohydrochloride monohydrate is 6.6%. As such, the measured value is consistent with the theoretical value.

| Batch | Chloride ion content (%) |
|---|---|
| 1 | 6.5% |
| 2 | 6.7% |
| 3 | 6.5% |
| 4 | 6.5% |
| 5 | 6.6% |

Experimental Example 9: Determination of the Water Content in the Sample by a Karl Fischer Method 50 mg of crystalline form I of compound A monohydrochloride monohydrate was taken and added to a Karl Fischer sample bottle. The sample bottle was sealed, and heated to 160° C. The water content was determined on a Metrohm KF 831 Coulometer through a coulometric heating furnace method. The water content in multiple batches of the samples as determined by this method was between 3.2% and 4.0%, while the theoretical water content of compound A monohydrochloride monohydrate is 3.3%. As such, the measured value is consistent with the theoretical value.

| Batch | Water content (%) |
|---|---|
| 1 | 3.6% |
| 2 | 3.7% |
| 3 | 3.5% |
| 4 | 4.0% |
| 5 | 3.2% |

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A salt of compound A,

Compound A

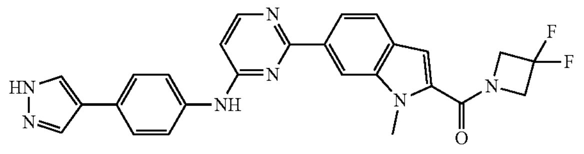

which is compound A monohydrochloride monohydrate, compound A monohydrochloride dihydrate, compound A monohydrochloride sesquihydrate, or compound A monohydrochloride mono-dimethyl sulfoxide complex.

2. The salt of compound A according to claim 1, wherein the compound A monohydrochloride monohydrate is in crystalline form I, and the crystalline form I has an XRPD pattern comprising characteristic peaks at diffraction angles (2θ) of 8.3±0.2°, 12.6±0.2° and 18.5±0.2°.

3. The salt of compound A according to claim 1, wherein the compound A monohydrochloride dihydrate is in crystalline form II, and the crystalline form II has an XRPD pattern comprising characteristic peaks at diffraction angles (2θ) of 9.9±0.2°, 13.2±0.2° and 16.2±0.2°.

4. The salt of compound A according to claim 1, wherein the compound A monohydrochloride sesquihydrate is in crystalline form Ill, and the crystalline form Ill has an XRPD pattern comprising characteristic peaks at diffraction angles (2θ) of 5.1±0.2°, 9.1±0.2° and 10.2±0.2°.

5. The salt of compound A according to claim 1, wherein the compound A monohydrochloride mono-dimethyl sulfoxide complex is in crystalline form IV, and the crystalline form IV has an XRPD pattern comprising characteristic peaks at diffraction angles (2θ) of 6.6±0.2°, 8.9±0.2° and 18.5±0.2°.

6. A pharmaceutical composition comprising the salt of compound A according to claim 1 and one or more pharmaceutically acceptable carriers.

7. A pharmaceutical composition comprising the salt of compound A according to claim 2 and one or more pharmaceutically acceptable carriers.

8. A pharmaceutical composition comprising the salt of compound A according to claim 3 and one or more pharmaceutically acceptable carriers.

9. A pharmaceutical composition comprising the salt of compound A according to claim 4 and one or more pharmaceutically acceptable carriers.

10. A pharmaceutical composition comprising the salt of compound A according to claim 5 and one or more pharmaceutically acceptable carriers.

* * * * *